US010155995B2

(12) United States Patent
Martignetti et al.

(10) Patent No.: US 10,155,995 B2
(45) Date of Patent: *Dec. 18, 2018

(54) **MUTATIONS IN *PDGFRB* AND *NOTCH3* AS CAUSES OF AUTOSOMAL DOMINANT INFANTILE MYOFIBROMATOSIS**

(71) Applicants: ICAHN SCHOOL OF MEDICINE AT MOUNT SINAI, New York, NY (US); THE CHILDREN'S HOSPITAL OF PHILADELPHIA, Philadelphia, PA (US)

(72) Inventors: John A. Martignetti, New York, NY (US); Hakon Hakonarson, Malvern, PA (US); Lifeng Tian, Philadelphia, PA (US)

(73) Assignees: ICAHN SCHOOL OF MEDICINE AT MOUNT SINAI, New York, NY (US); THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/788,947

(22) Filed: Oct. 20, 2017

(65) Prior Publication Data

US 2018/0223373 A1 Aug. 9, 2018

Related U.S. Application Data

(63) Continuation of application No. 14/786,425, filed as application No. PCT/US2014/035000 on Apr. 22, 2014, now Pat. No. 9,822,418.

(60) Provisional application No. 61/814,439, filed on Apr. 22, 2013.

(51) Int. Cl.
| | |
|---|---|
| *C12Q 1/68* | (2018.01) |
| *A61K 31/506* | (2006.01) |
| *A61K 45/06* | (2006.01) |
| *A61N 5/00* | (2006.01) |
| *C12Q 1/6883* | (2018.01) |
| *C12Q 1/6886* | (2018.01) |

(52) U.S. Cl.
CPC .......... *C12Q 1/6886* (2013.01); *A61K 31/506* (2013.01); *A61K 45/06* (2013.01); *A61N 5/00* (2013.01); *C12Q 1/6883* (2013.01); *C12Q 2600/156* (2013.01)

(58) Field of Classification Search
None
See application file for complete search history.

(56) References Cited

U.S. PATENT DOCUMENTS 9,822,418 B2 * 11/2017 Martignetti .......... C12Q 1/6883
2015/0316552 A1 11/2015 Cain et al.

OTHER PUBLICATIONS

Andrae et al., "Role of platelet-derived growth factors in physiology and medicine," *Genes Dev.*, 22(10):1276-1312, 2008.
Apasricio-Gallego et al., "New insights into molecular mechanisms of sunitinib-associated side effects," *Mol. Cancer Ther.*, 10(12):2215-2223, 2011.
Arts et al., "PDGFRB gain-of-function mutations in sporadic infantile myofibromatosis," *Hum. Mol. Genet.*, 26(10):1801-1810, 2017.
Arts et al., "PDGFRB mutants found in patients with familial infantile myofibromatosis or overgrowth syndrome are oncogenic and sensitive to imatinib," *Oncogene*, 35(25):3239-48, 2016.
Cheung et al., "A recurrent PDGFRB mutation causes familial infantile myofibromatosis," *Am. J. Hum. Genet.*, 92(6):996-1000, 2013.
Extended European Search Report issued in European Patent Application No. 14787679.1, dated Dec. 16, 2016.
Fouillade et al., "Activating NOTCH3 mutation in a patient with Small-vessel-disease of the brain," *Hum. Mutat.*, 29(3):452, 2008.
Franzese et al., "Infantile myofibromatosis: unusual diagnosis in an older child," *International Journal of Pediatric Otorhinolaryngology*, 69(6):865-868, 2005.
Ikediobi et al., "Infantile myofibromatosis: support for autosomal dominant inheritance," *J. Am Acad. Dermatol.*, 49(2 Suppl.Case Reports):S148-S150, 2003.
Jennings et al., "Infantile myofibromatosis. Evidence for an autosomal-dominant disorder," *Am. J. Surg. Pathol.*, 8(7):529-538, 1984.
Jin et al., "Notch signaling regulates platelet-derived growth factor receptor-beta expression in vascular smooth muscle cells," *Circ. Res.*, 102(12):1483-1491, 2008.
Joutel et al., "Notch3 mutations in CADASIL, a hereditary adult-onset condition causing stroke and dementia," *Nature*, 383(6602):707-710, 1996.
Lee, "Mutations in PDGFRB and NOTCH3 are the first genetic causes identified for autosomal dominant infantile myofibromatosis," *Clinical Genetics*, 84(4):340-341, 2013.
Lepelletier et al., "Heterozygous PDGFRB Mutation in a Three-generation Family with Autosomal Dominant Infantile Myofibromatosis," *Acta Derm. Venereol.*, DOI: 10.2340/00015555-2671, 2017.

(Continued)

*Primary Examiner* — Michael Barker
(74) *Attorney, Agent, or Firm* — Parker Highlander PLLC

(57) ABSTRACT

This invention relates to a method of diagnosing a subject as having and/or being a carrier for infantile myofibromatosis. This method involves providing an isolated biological sample from a subject; contacting the sample with one or more reagents suitable for detecting the presence or absence of one or more mutations in PDGFRB and/or NOTCH3; detecting, in the sample, the presence or absence of the one or more mutations in PDGFRB and/or NOTCH3 based on said contacting; and diagnosing the subject as having and/or being a carrier for infantile myofibromatosis based on said detecting, where the presence of the one or more mutations in PDGFRB and/or NOTCH3 indicates the subject has a mutation that causes infantile myofibromatosis. Also disclosed is a method of treating a subject having infantile myofibromatosis and a method of preventing or treating symptoms associated with infantile myofibromatosis.

13 Claims, 7 Drawing Sheets

Specification includes a Sequence Listing.

(56) References Cited

OTHER PUBLICATIONS

Martignetti et al., "Mutations in PDGFRB cause autosomal-dominant infantile myofibromatosis," *Am. J. Hum. Genet.*, 92(6):1001-1007, 2013.

Mudry et al., "Case report: rapid and durable response to PDGFR targeted therapy in a child with refractory multiple infantile myofibromatosis and a heterozygous germline mutation of the PDGFRB gene," *BMC Cancer*, 17(1):119, 2017.

Murray et al., "The spectrum of infantile myofibromatosis includes both non-penetrance and adult recurrence," *Eur. J. Med. Genet.*, 60(7):353-358, 2017.

Narchi, "Four half-siblings with infantile myofibromatosis: a case for autosomal-recessive inheritance," *Clinical Genetics*, 59(2):134-135, 2001.

Nicolas et al., "Mutation of the PDGFRB gene as a cause of idiopathic basal ganglia calcification," *Neurology*, 80(2):181-7, 2013.

Office Communication issued in U.S. Appl. No. 14/786,425, dated Nov. 28, 2016.

PCT International Search Report and Written Opinion issued in International Application No. PCT/US2014/035000, dated Oct. 1, 2014.

Smith et al., "Infantile myofibromatosis: Two families supporting autosomal dominant inheritance," *Australian Journal of Dermatology*, 52(3):214-217, 2011.

Vanlandewijck et al., "Functional Characterization of Germline Mutations in PDGFB and PDGFRB in Primary Familial Brain Calcification," *PLOS ONE*, 10(11):e0143407, DOI: 10.1371/journal.pone.0143407, eCollection, 2015.

Zand et al., "Autosomal dominant inheritance of infantile myofibromatosis," *Am. J. Med. Genet. Part A*, 126A(3):261-266, 2004.

\* cited by examiner

FIGs. 2A-B

| Gene (MIM) | Genomic Location (hg19) RefSeq | Exon | Famiy | cDNA | Protein | MAF in 1000 genomes project or ESP6500SI |
|---|---|---|---|---|---|---|
| *PDGFRB* (173410) | chr5:149503858 NM 002609.3 | 14 | IM1 | c.1978C>A | Pro660Thr | 0.000077 |
| *PDGFRB* (173410) | chr5: 149505134 NM 002609.3 | 12 | IM2-8 | c.1681C>T | Arg561Cys | - |
| *NOTCH3* (600276) | chr19: 15285059 NM 000435.2 | 25 | IM9 | c.4556T>C | Leu1519Pro | - |

|  | IM-1 | IM-2 | IM-3 | IM-4 | IM-5 | IM-6 | IM-7 | IM-8 | IM-9-III-1 | IM-9-III-4 | IM-9-III-9 |
|---|---|---|---|---|---|---|---|---|---|---|---|
| Heterozygous NS/SS/I | 7478 | 7823 | 7788 | 7775 | 7508 | 7569 | 7357 | 7555 | 8043 | 8038 | 7784 |
| Rare | 144 | 170 | 176 | 169 | 158 | 162 | 168 | 177 | 150 | 145 | 138 |
| Deleterious | 35 | 33 | 31 | 31 | 37 | 30 | 30 | 31 | 31 | 30 | 30 |
| PDGFRB | 1 | 1 | 1 | 1 | 1 | 1 | 1 | 1 | 0 | 0 | 0 |
| NOTCH3 | 0 | 0 | 0 | 0 | 0 | 0 | 0 | 0 | 1 | 1 | 1 |
| PET112 | 0 | 0 | 0 | 0 | 0 | 0 | 0 | 0 | 1 | 1 | 1 |

MUTATIONS IN *PDGFRB* AND *NOTCH3* AS CAUSES OF AUTOSOMAL DOMINANT INFANTILE MYOFIBROMATOSIS

This application is a continuation application of U.S. patent application Ser. No. 14/786,425, filed Oct. 22, 2015, now U.S. Pat. No. 9,822,418, which is a national phase application under 35 U.S.C. § 371 of International Application No. PCT/US2014/035000, filed Apr. 22, 2014, which claims the priority benefit of U.S. Provisional Application Ser. No. 61/814,439, filed Apr. 22, 2013. The entire contents of the above-referenced disclosures are specifically incorporated herein by reference.

Pursuant to 37 C.F.R. 1.821(c), a sequence listing is submitted herewith as an ASCII compliant text file named "CHOPP0002USD1_ST25.txt", created on Oct. 13, 2017 and having a size of ~49 kilobytes. The content of the aforementioned file is hereby incorporated by reference in its entirety.

FIELD OF THE INVENTION

The present invention relates to methods of diagnosis, treatment, and prevention of infantile myofibromatosis.

BACKGROUND OF THE INVENTION

Infantile myofibromatosis (MIM 228550) ("IM") is one of the most common proliferative fibrous tumors of infancy and childhood. First described by Williams et al., "Congenital Fibrosarcoma: Report of a Case in a Newborn Infant," *AMA Arch. Pathl.* 51:548-552 (1951) and Stout (Stout, "Juvenile Fibromatoses," *Cancer* 7:953-978 (1954)), IM was further sub-categorized by others into solitary, multiple or generalized forms and shown to affect the skin, muscle, bone, and viscera (Kauffman et al., "Congenital Mesenchymal Tumors," *Cancer* 18:460-476 (1965)). The term "infantile myofibromatosis" was recommended based on the fact that the cells have features of both differentiated fibroblasts and smooth muscle cells (myofibroblasts) (Chung et al., "Infantile Myofibromatosis," *Cancer* 48:1807-1818 (1981)). Soft tissue lesions usually arise during childhood but can arise at any time during life and, intriguingly, can regress spontaneously. On the other hand, visceral lesions are associated with high morbidity and mortality (Wiswell et al., "Infantile Myofibromatosis: The Most Common Fibrous Tumor of Infancy," *J. Pediatr. Surg.* 23:315-318 (1988)). The mechanism(s) underlying tumor growth and regression are not known. Some have suggested tumor growth to be linked to angiogenic stimulation and regression (Leaute-Labreze et al., "A Self-healing Generalized Infantile Myofibromatosis with Elevated Urinary bFGF," *Ped. Derm.* 18:305-307 (2001)). Indeed, in a single case report, regression of an intracardiac IM was achieved through use of interferon alpha-2b (Auriti et al., "Remission of Infantile Generalized Myofibromatosis After Interferon Alpha Therapy," *J. Pediatr. Hematol. Oncol.* 30:179-181 (2008)).

The genetic etiology of IM is unknown and both autosomal recessive ("AR") and dominant ("AD") patterns of inheritance have been reported. Consanguinity in a number of pedigrees has been interpreted to be in accord with an AR pattern of inheritance (Baird et al., "Congenital Generalized Fibromatosis: An Autosomal Recessive Condition?" *Clin. Genet.* 9:488-494 (1976); Salamah et al., "Infantile Myofibromatosis," *J. Pediatr. Surg.* 23:975-977 (1988); Narchi, "Four Half-Siblings with Infantile Myofibromatosis: A Case for Autosomal-Recessive Inheritance," *Clin. Genet.* 59:134-135 (2001)). A large number of pedigrees, where affected individuals are identified across generations, are consistent with IM being an AD disease (Bartlett et al., "Multiple Congenital Neoplasms of Soft Tissues: Report of 4 Cases in 1 Family," *Cancer* 14:913-920 (1960); Pfluger et al., "Kongenitale Polyfibromatose: Klinische and Genetische Untersuchungen," *Wiener Klinishe Wochenshrift* 88:92-94 (1976); Jennings et al., "Infantile Myofibromatosis: Evidence for an Autosomal-dominant Disorder," *Am. J. Surg. Pathol.* 8:529-538 (1984); Ikediobi et al., "Infantile Myofibromatosis: Support for Autosomal Dominant Inheritance," *J. Am. Acad. Dermatol.* 49:S148-150 (2003); Zand et al., "Autosomal Dominant Inheritance of Infantile Myofibromatosis," *Am. J. Med. Genet. A.* 126:261-266 (2004); de Montpréville et al., "Endocardial Location of Familial Myofibromatosis Revealed by Cerebral Embolization: Cardiac Counterpart of the Frequent Intravascular Growth of the Disease?" *Virchows Arch.* 444:300-303 (2004); Smith et al., "Infantile Myofibromatosis: Two Families Supporting Autosomal Dominant Inheritance," *Australas J. Dermatol.* 52:214-217 (2011); Kulkarni et al., "Infantile Myofibromatosis: Report on a Family with Autosomal Dominant Inheritance and Variable Penetrance," *J. Pediatr. Surg.* 47:2312-2315 (2012)).

The present invention is directed to overcoming deficiencies in the art.

SUMMARY OF THE INVENTION

One aspect of the present invention relates to a method of diagnosing a subject as having and/or being a carrier for infantile myofibromatosis. This method involves providing an isolated biological sample from a subject; contacting the sample with one or more reagents suitable for detecting the presence or absence of one or more mutations in PDGFRB and/or NOTCH3; detecting, in the sample, the presence or absence of the one or more mutations in PDGFRB and/or NOTCH3 based on said contacting; and diagnosing the subject as having and/or being a carrier for infantile myofibromatosis based on said detecting, where the presence of the one or more mutations in PDGFRB and/or NOTCH3 indicates the subject has a mutation that causes infantile myofibromatosis.

Another aspect of the present invention relates to a method of treating a subject having infantile myofibromatosis. This method involves selecting a subject having one or more mutations in PDGFRB and/or NOTCH3 and administering a therapy suitable for treating infantile myofibromatosis to the selected subject.

A further aspect of the present invention relates to a method of preventing or treating symptoms associated with infantile myofibromatosis. This method involves selecting a subject having one or more mutations in PDGFRB and/or NOTCH3 and administering to the selected subject an agent that modulates PDGFRB and/or NOTCH3 gene expression and/or PDGFRB and/or NOTCH3 encoded protein activity under conditions effective to prevent or treat symptoms associated with infantile myofibromatosis in the subject.

Another aspect of the present invention relates to a method of diagnosing a subject as having and/or being a carrier for infantile myofibromatosis. This method involves providing an isolated biological sample from a subject. The sample is contacted with one or more reagents suitable for detecting PDGFRB and/or NOTCH3 RNA and/or protein levels. Levels of PDGFRB and/or NOTCH3 RNA and/or protein are detected in the sample based on said contacting. The subject is diagnosed as having and/or being a carrier for infantile myofibromatosis based on said detecting, where decreased levels of PDGFRB and/or NOTCH3 RNA and/or protein compared to normal levels of PDGFRB and/or NOTCH3 RNA and/or protein indicates the subject has or is a carrier for infantile myofibromatosis.

A further aspect of the present invention relates to a method of treating a subject having infantile myofibromatosis. This method involves selecting a subject having decreased levels of PDGFRB and/or NOTCH3 RNA and/or protein compared to a subject having normal levels of PDGFRB and/or NOTCH3 RNA and/or protein and administering a therapy suitable for treating infantile myofibromatosis to the selected subject.

Another aspect of the present invention relates to a method of preventing or treating symptoms associated with infantile myofibromatosis. This method involves selecting a subject having decreased levels of PDGFRB and/or NOTCH3 RNA and/or protein compared to a subject having normal levels of PDGFRB and/or NOTCH3 RNA and/or protein. An agent that modulates PDGFRB and/or NOTCH3 gene expression and/or PDGFRB and/or NOTCH3 encoded protein activity is administered to the selected subject under conditions effective to prevent or treat symptoms associated with infantile myofibromatosis in the subject.

A further aspect of the present invention relates to a method of treating a subject having infantile myofibromatosis. This method involves selecting a subject having a mutation in PDGFRB encoding an amino acid substitution at one or more amino acid residues corresponding to amino acid position 561 and/or 660 of SEQ ID NO:2. The method further involves administering to the selected subject an agent that reduces phosphorylation of PDGFRB under conditions effective to prevent or treat symptoms associated with infantile myofibromatosis in the subject.

As described herein in the Examples, IM gene(s) were identified using whole-exome sequencing on members of nine unrelated IM families, five who have been previously reported (see Jennings et al., "Infantile Myofibromatosis: Evidence for an Autosomal-dominant Disorder," *Am. J. Surg. Pathol.* 8:529-538 (1984); Ikediobi et al., "Infantile Myofibromatosis: Support for Autosomal Dominant Inheritance," *J. Am. Acad. Dermatol.* 49:S148-150 (2003); Zand et al., "Autosomal Dominant Inheritance of Infantile Myofibromatosis," *Am. J. Med. Genet. A.* 126:261-266 (2004); de Montpréville et al., "Endocardial Location of Familial Myofibromatosis Revealed by Cerebral Embolization: Cardiac Counterpart of the Frequent Intravascular Growth of the Disease?" *Virchows Arch.* 444:300-303 (2004)), and four new families, all whose family histories were consistent with autosomal dominant inheritance. The present invention relates to the identification of two IM genes, both involved in activating multiple cellular functions including differentiation, proliferation, and survival, both expressed in vascular smooth muscle cells and one gene product able to activate the other. Specifically, two missense mutations in the cell surface tyrosine kinase receptor PDGFRB (c.1978C>A [p.Pro660Tyr] and c.1681C>T [p.Arg561Cys]), and one missense mutation in the single pass transmembrane protein NOTCH3 (c.4556T>C, p.Leu1519Pro) were identified.

BRIEF DESCRIPTION OF THE DRAWINGS

FIG. 2A provides plots illustrating representative sequence chromatograms for each of the different mutations identified. FIG. 2B illustrates the conservation of the mutations and the surrounding region in vertebrates. Arrowheads indicate the positions of the mutated alleles.

FIG. 3 is a table showing the results of exome sequencing in which three missense mutations have been identified in two genes causing autosomal dominant IM in nine unrelated families, i.e., c.1978C>A (p.Pro660Thr) and c.1681C>T (p.Arg561Cys) in PDGFRB, and c.4556T>C (p.Leu1519Pro) in NOTCH3.

DETAILED DESCRIPTION OF THE INVENTION

Figure 1:
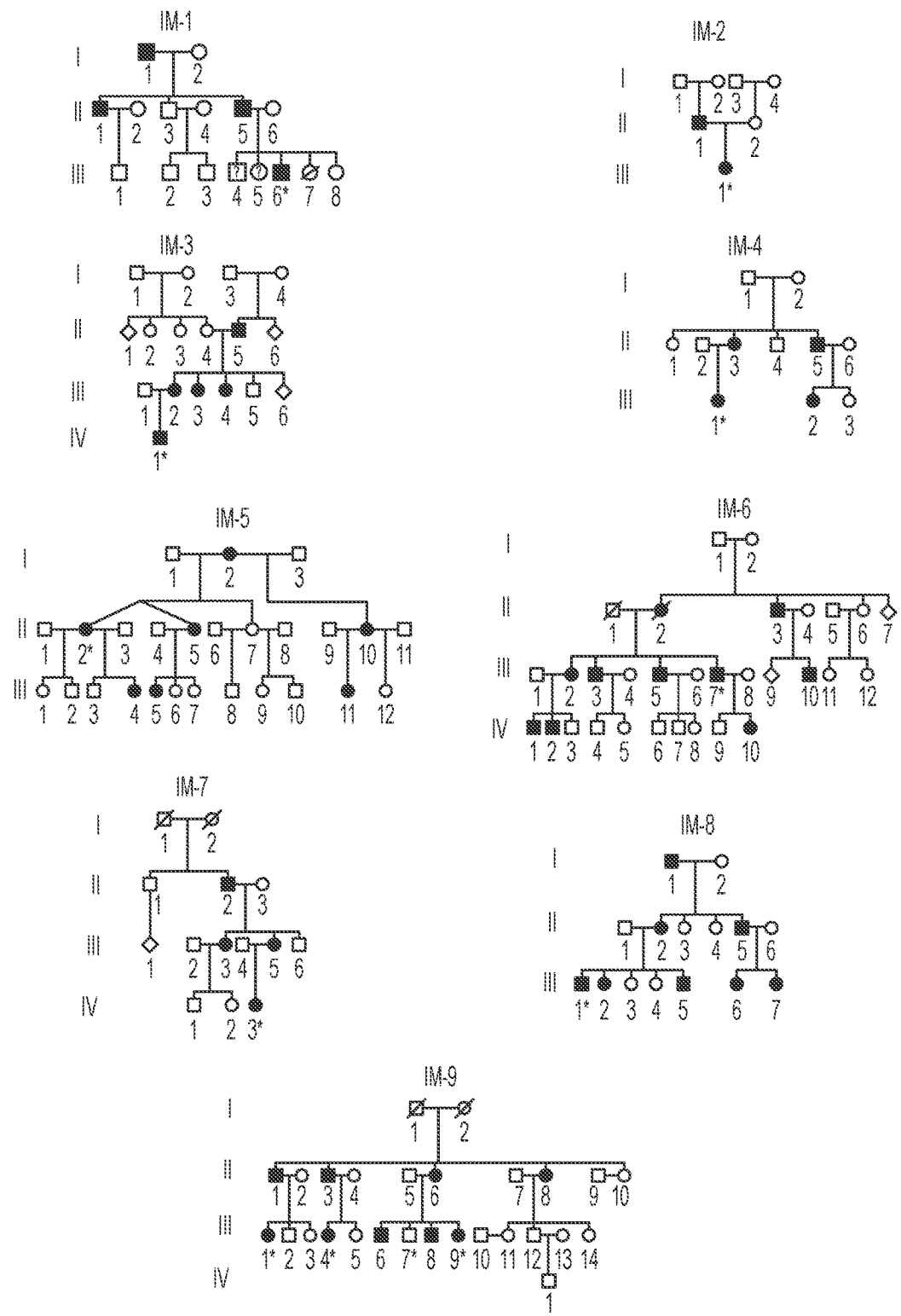
FIG. 1 illustrates the pedigrees of nine unrelated IM families. The inheritance pattern in all the families used in the Examples described herein was consistent with autosomal dominant transmission. Five families have been previously reported, i.e., IM-1 (Jennings et al., "Infantile Myofibromatosis: Evidence for an Autosomal-Dominant Disorder," *Am. J. Surg. Pathol.* 8:529-538 (1984), which is hereby incorporated by reference in its entirety), IM-2 (Ikediobi et al., "Infantile Myofibromatosis: Support for Autosomal Dominant Inheritance," *J. Am. Acad. Dermatol.* 49:S148-150 (2003), which is hereby incorporated by reference in its entirety), IM-6 (Zand et al., "Autosomal Dominant Inheritance of Infantile Myofibromatosis," *Am. J. Med. Genet. A.* 126:261-266 (2004), which is hereby incorporated by reference in its entirety), IM-7 (Zand et al., "Autosomal Dominant Inheritance of Infantile Myofibromatosis," *Am. J. Med. Genet. A.* 126:261-266 (2004), which is hereby incorporated by reference in its entirety), and IM-8 (de Montpréville et al., "Endocardial Location of Familial Myofibromatosis Revealed by Cerebral Embolization: Cardiac Counterpart of the Frequent Intravascular Growth of the Disease?" *Virchows Arch.* 444:300-303 (2004), which is hereby incorporated by reference in its entirety). *These samples were whole-exome sequenced.

The present invention relates to the identification of genes associated with an autosomal dominant inheritance pattern of infantile myofibromatosis. In a first aspect, the present invention relates to a method of diagnosing a subject as having and/or being a carrier for infantile myofibromatosis. This method involves providing an isolated biological sample from a subject; contacting the sample with one or more reagents suitable for detecting the presence or absence of one or more mutations in PDGFRB and/or NOTCH3; detecting, in the sample, the presence or absence of the one or more mutations in PDGFRB and/or NOTCH3 based on said contacting; and diagnosing the subject as having and/or being a carrier for infantile myofibromatosis based on said detecting, where the presence of the one or more mutations in PDGFRB and/or NOTCH3 indicates the subject has a mutation that causes infantile myofibromatosis.

According to the present invention, mutations in PDGFRB and NOTCH3 have been identified that predict that a subject is a carrier for or has infantile myofibromatosis. Specifically, detecting in a biological sample from a subject the presence of one or more of these mutations, predicts that the subject is a carrier for or has infantile myofibromatosis.

Thus, according to this aspect of the present invention, an isolated biological sample from a subject is provided. The biological sample may be any sample containing genetic information about the PDGFRB and/or NOTCH3 gene of the subject. In one embodiment, the sample is a blood sample from the subject.

In carrying out this method, once the isolated biological sample is isolated, the sample is contacted with one or more reagents suitable for detecting the presence or absence of one or more mutations in PDGFRB and/or NOTCH3. Suitable reagents will depend on the particular mutation being detected, and the particular method of detecting the mutation, which are now described as follows.

In one embodiment, the one or more mutations detected in a biological sample from a subject includes mutations specific to the PDGFRB gene. The mRNA and amino acid sequences for human PDGFRB are provided in GenBank Accession No. NM_002609, and as SEQ ID NO:1 and SEQ ID NO:2, respectively as set forth below.

The cDNA sequence of PDGFRB is SEQ ID NO:1, as follows:

```
ctcctgaggc tgccagcagc cagcagtgac
tgcccgccct atctgggacc caggatcgct
ctgtgagcaa cttggagcca gagaggagat
caacaaggag gaggagagag ccggcccctc
agccctgctg cccagcagca gcctgtgctc
gccctgccca acgcagacag ccagacccag
ggcggcccct ctggcggctc tgctcctccc
gaaggatgct tggggagtga ggcgaagctg
ggccgctcct ctcccctaca gcagcccct
tcctccatcc ctctgttctc ctgagccttc
aggagcctgc accagtcctg cctgtccttc
tactcagctg ttacccactc tgggaccagc
agtctttctg ataactggga gagggcagta
aggaggactt cctggagggg gtgactgtcc
agagcctgga actgtgccca caccagaagc
catcagcagc aaggacacca tgcggcttcc
gggtgcgatg ccagctctgg ccctcaaagg
cgagctgctg ttgctgtctc tcctgttact
```

```
tctggaacca cagatctctc agggcctggt
cgtcacaccc ccggggccag agcttgtcct
caatgtctcc agcaccttcg ttctgacctg
ctcgggttca gctccggtgg tgtgggaacg
gatgtcccag gagcccccac aggaaatggc
caaggcccag gatggcacct tctccagcgt
gctcacactg accaacctca ctgggctaga
cacgggagaa tacttttgca cccacaatga
ctcccgtgga ctggagaccg atgagcgaaa
acggctctac atctttgtgc cagatcccac
cgtgggcttc ctccctaatg atgccgagga
actattcatc tttctcacgg aaataactga
gatcaccatt ccatgccgag taacagaccc
acagctggtg gtgacactgc acgagaagaa
aggggacgtt gcactgcctg tccctatga
tcaccaacgt ggcttttctg gtatctttga
ggacagaagc tacatctgca aaaccaccat
tgggacagg gaggtggatt ctgatgccta
ctatgtctac agactccagg tgtcatccat
caacgtctct gtgaacgcag tgcagactgt
ggtccgccag ggtgagaaca tcacctctca t
gtgcattgtg atcgggaatg aggtggtcaa
cttcgagtgg acataccccc gcaaagaaag
tgggcggctg gtggagccgg tgactgactt
cctcttggat atgccttacc acatccgctc
catcctgcac atccccagtg ccgagttaga
agactcgggg acctacacct gcaatgtgac
ggagagtgtg aatgaccatc aggatgaaaa
ggccatcaac atcaccgtgg ttgagagcgg
ctacgtgcgg ctcctgggag aggtgggcac
actacaattt gctgagctgc atcggagccg
gacactgcag gtagtgttcg aggcctaccc
accgcccact gtcctgtggt tcaaagacaa
ccgcaccctg ggcgactcca gcgctggcga
aatcgccctg tccacgcgca acgtgtcgga
gacccggtat gtgtcagagc tgacactggt
tcgcgtgaag gtggcagagg ctggccacta
caccatgcgg gccttccatg aggatgctga
ggtccagctc tccttccagc tacagatcaa
tgtccctgtc cgagtgctgg agctaagtga
gagccacct gacagtgggg aacagacagt
```

-continued

```
ccgctgtcgt ggccggggca tgccccagcc
gaacatcatc tggtctgcct gcagagacct
caaaaggtgt ccacgtgagc tgccgcccac
gctgctggga aacagttccg aagaggagag
ccagctggag actaacgtga cgtactggga
ggaggagcag gagtttgagg tggtgagcac
actgcgtctg cagcacgtgg atcggccact
gtcggtgcgc tgcacgctgc gcaacgctgt
gggccaggac acgcaggagg tcatcgtggt
gccacactcc ttgcccttta aggtggtggt
gatctcagcc atcctggccc tggtggtgct
caccatcatc tcccttatca tcctcatcat
gctttggcag aagaagccac gttacgagat
ccgatggaag gtgattgagt ctgtgagctc
tgacggccat gagtacatct acgtggaccc
catgcagctg ccctatgact ccacgtggga
gctgccgcgg gaccagcttg tgctgggacg
caccctcggc tctgggggcct ttgggcaggt
ggtggaggcc acggctcatg gcctgagcca
ttctcaggcc acgatgaaag tggccgtcaa
gatgcttaaa tccacagccc gcagcagtga
gaagcaagcc cttatgtcgg agctgaagat
catgagtcac cttgggcccc acctgaacgt
ggtcaacctg ttggggggcct gcaccaaagg
aggacccatc tatatcatca ctgagtactg
ccgctacgga gacctggtgg actacctgca
ccgcaacaaa cacaccttcc tgcagcacca
ctccgacaag cgccgcccgc ccagcgcgga
gctctacagc aatgctctgc ccgttgggct
ccccctgccc agccatgtgt ccttgaccgg
ggagagcgac ggtggctaca tggacatgag
caaggacgag tcggtggact atgtgcccat
gctggacatg aaaggagacg tcaaatatgc
agacatcgag tcctccaact acatggcccc
ttacgataac tacgttccct ctgcccctga
gaggacctgc gagcaactt tgatcaacga
gtctccagtg ctaagctaca tggacctcgt
gggcttcagc taccaggtgg ccaatggcat
ggagtttctg cctccaaga actgcgtcca
cagagacctg gcggctagga acgtgctcat
```

-continued

```
ctgtgaaggc aagctggtca agatctgtga
ctttggcctg gctcgagaca tcatgcggga
ctcgaattac atctccaaag gcagcacctt
tttgccttta aagtggatgg ctccggagag
catcttcaac agcctctaca ccaccctgag
cgacgtgtgg tccttcggga tcctgctctg
ggagatcttc accttgggtg gccccctta
cccagagctg cccatgaacg agcagttcta
caatgccatc aaacggggtt accgcatggc
ccagcctgcc catgcctccg acgagatcta
tgagatcatg cagaagtgct gggaagagaa
gttttgagatt cggccccccct ctcccagct
ggtgctgctt ctcgagagac tgttgggcga
aggttacaaa aagaagtacc agcaggtgga
tgaggagttt ctgaggagtg accacccagc
catccttcgg tcccaggccc gcttgcctgg
gttccatggc ctccgatctc ccctggacac
cagctccgtc ctctatactg ccgtgcagcc
caatgagggt gacaacgact atatcatccc
cctgcctgac cccaaacccg aggttgctga
cgagggccca ctgagggtt cccccagcct
agccagctcc accctgaatg aagtcaacac
ctcctcaacc atctcctgtg acagccccct
ggagccccag gacgaaccag agccagagcc
ccagcttgag ctccaggtgg agccggagcc
agagctggaa cagttgccgg attcgggtg
ccctgcgcct cgggcggaag cagaggatag
cttcctgtag ggggctggcc cctaccctgc
cctgcctgaa gctccccccc tgccagcacc
cagcatctcc tggcctggcc tgaccgggct
tcctgtcagc caggctgccc ttatcagctg
tccccttctg gaagctttct gctcctgacg
tgttgtgccc caaaccctgg ggctggctta
ggaggcaaga aaactgcagg ggccgtgacc
agccctctgc ctccagggag gccaactgac
tctgagccag ggttccccca gggaactcag
ttttcccata tgtaagatgg gaaagttagg
cttgatgacc cagaatctag gattctctcc
ctggctgaca ggtggggaga ccgaatccct
ccctgggaag attcttggag ttactgaggt
ggtaaattaa cttttttctg ttcagccagc
```

```
taccccctcaa ggaatcatag ctctctcctc
gcactttat ccacccagga gctagggaag
agaccctagc ctccctggct gctggctgag
ctaggccta gccttgagca gtgttgcctc
atccagaaga aagccagtct cctccctatg
atgccagtcc ctgcgttccc tggcccgagc
tggtctgggg ccattaggca gcctaattaa
tgctggaggc tgagccaagt acaggacacc
cccagcctgc agcccttgcc cagggcactt
ggagcacacg cagccatagc aagtgcctgt
gtccctgtcc ttcaggccca tcagtcctgg
ggcttttct ttatcaccct cagtcttaat
ccatccacca gagtctagaa ggccagacgg
gccccgcatc tgtgatgaga atgtaaatgt
gccagtgtgg agtggccacg tgtgtgtgcc
agtatatggc cctggctctg cattggacct
gctatgaggc tttggaggaa tccctcaccc
tctctgggcc tcagtttccc cttcaaaaaa
tgaataagtc ggacttatta actctgagtg
ccttgccagc actaacattc tagagtattc
caggtggttg cacatttgtc cagatgaagc
aaggccatat acctaaact tccatcctgg
gggtcagctg ggctcctggg agattccaga
tcacacatca cactctgggg actcaggaac
catgcccctt ccccaggccc cagcaagtc
tcaagaacac agctgcacag gccttgactt
agagtgacag ccggtgtcct ggaaagcccc
cagcagctgc cccagggaca tgggaagacc
acgggacctc tttcactacc cacgatgacc
tccgggggta tcctgggcaa aagggacaaa
gagggcaaat gagatcacct cctgcagccc
accactccag cacctgtgcc gaggtctgcg
tcgaagacag aatggacagt gaggacagtt
atgtcttgta aaagacaaga agcttcagat
gggtacccca agaaggatgt gagaggtggg
cgctttggag gtttgcccct cacccaccag
ctgccccatc cctgaggcag cgctccatgg
gggtatggtt ttgtcactgc ccagacctag
cagtgacatc tcattgtccc cagcccagtg
ggcattggag gtgccagggg agtcagggt
gtagccaaga cgccccgca cggggagggt
tgggaagggg gtgcaggaag ctcaacccct
ctgggcacca accctgcatt gcaggttggc
accttacttc cctgggatcc ccagagttgg
tccaaggagg gagagtgggt tctcaatacg
gtaccaaaga tataatcacc taggtttaca
aatatttta ggactcacgt taactcacat
ttatacagca gaaatgctat tttgtatgct
gttaagtttt tctatctgtg tactttttt
taagggaaag atttaatat taaacctggt
gcttctcact cacaaaaa
```

The amino acid sequence encoded by PDGFRB is SEQ ID NO:2, as follows:

```
MRLPGAMPAL ALKGELLLLS LLLLLEPQIS QGLVVTPPGP
ELVLNVSSTF VLTCSGSAPV VWERMSQEPP QEMAKAQDGT
FSSVLTLTNL TGLDTGEYFC THNDSRGLET DERKRLYIFV
PDPTVGFLPN DAEELFIFLT EITEITIPCR VTDPQLVVTL
HEKKGDVALP VPYDHQRGFS GIFEDRSYIC KTTIGDREVD
SDAYYVYRLQ VSSINVSVNA VQTVVRQGEN ITLMCIVIGN
EVVNFEWTYP RKESGRLVEP VTDFLLDMPY HIRSILHIPS
AELEDSGTYT CNVTESVNDH QDEKAINITV VESGYVRLLG
EVGTLQFAEL HRSRTLQVVF EAYPPPTVLW FKDNRTLGDS
SAGEIALSTR NVSETRYVSE LTLVRVKVAE AGHYTMRAFH
EDAEVQLSFQ LQINVPVRVL ELSESHPDSG EQTVRCRGRG
MPQPNIIWSA CRDLKRCPRE LPPTLLGNSS EEESQLETNV
TYWEEEQEFE VVSTLRLQHV DRPLSVRCTL RNAVGQDTQE
VIVVPHSLPF KVVVISAILA LVVLTIISLI ILIMLWQKKP
RYEIRWKVIE SVSSDGHEYI YVDPMQLPYD STWELPRDQL
VLGRTLGSGA FGQVVEATAH GLSHSQATMK VAVKMLKSTA
RSSEKQALMS ELKIMSHLGP HLNVVNLLGA CTKGGPIYII
TEYCRYGDLV DYLHRNKHTF LQHHSDKRRP PSAELYSNAL
PVGLPLPSHV SLTGESDGGY MDMSKDESVD YVPMLDMKGD
VKYADIESSN YMAPYDNYVP SAPERTCRAT LINESPVLSY
MDLVGFSYQV ANGMEFLASK NCVHRDLAAR NVLICEGKLV
KICDFGLARD IMRDSNYISK GSTFLPLKWM APESIFNSLY
TTLSDVWSFG ILLWEIFTLG GTPYPELPMN EQFYNAIKRG
YRMAQPAHAS DEIYEIMQKC WEEKFEIRPP FSQLVLLLER
LLGEGYKKKY QQVDEEFLRS DHPAILRSQA RLPGFHGLRS
PLDTSSVLYT AVQPNEGDND YIIPLPDPKP EVADEGPLEG
SPSLASSTLN EVNTSSTISC DSPLEPQDEP EPEPQLELQV
EPEPELEQLP DSGCPAPRAE AEDSFL
```

Specific mutations in PDGFRB which are indicative of having IM and/or being an autosomal dominant carrier of IM include amino acid substitutions at one or more amino acid residues corresponding to amino acid positions 561 and/or 660 of SEQ ID NO:2.

According to one embodiment, the amino acid substitution comprises an arginine to cysteine substitution at the amino acid position corresponding to Arg561 of SEQ ID NO:2.

According to another embodiment, the amino acid substitution comprises a proline to threonine substitution at the amino acid position corresponding to Pro660 of SEQ ID NO:2.

In one embodiment, the one or more mutations detected in a biological sample from a subject includes one or more mutations specific to the NOTCH3 gene. The mRNA and amino acid sequences for human NOTCH3 are provided in GenBank Accession No. NM_000435, and as SEQ ID NO:3 and SEQ ID NO:4, respectively as set forth below.

The cDNA sequence of NOTCH3 is SEQ ID NO:3, as follows:

```
gcggcgcgga ggctggcccg ggacgcgccc
ggagcccagg gaaggaggga ggaggggagg
gtcgcggccg gccgccatgg ggccgggggc
ccgtggccgc cgccgccgcc gtcgcccgat
gtcgccgcca ccgccaccgc cacccgtgcg
ggcgctgccc ctgctgctgc tgctagcggg
gccgggggct gcagcccccc cttgcctgga
cggaagcccg tgtgcaaatg gaggtcgttg
cacccagctg ccctcccggg aggctgcctg
cctgtgcccg cctggctggg tgggtgagcg
gtgtcagctg gaggacccct gtcactcagg
cccctgtgct ggccgtggtg tctgccagag
ttcagtggtg gctggcaccg cccgattctc
atgccggtgc ccccgtggct tccgaggccc
tgactgctcc ctgccagatc cctgcctcag
cagcccttgt gcccacggtg cccgctgctc
agtggggccc gatggacgct tcctctgctc
ctgcccacct ggctaccagg gccgcagctg
ccgaagcgac gtggatgagt gccgggtggg
tgagccctgc cgccatggtg gcacctgcct
caacacacct ggctccttcc gctgccagtg
tccagctggc tacacagggc cactatgtga
gaacccgcg gtgccctgtg cacc ctcacc
atgccgtaac gggggcacct gcaggcagag
tggcgacctc acttacgact gtgcctgtct
tcctgggttt gagggtcaga attgtgaagt
gaacgtggac gactgtccag gacaccgatg
tctcaatggg gggacatgcg tggatggcgt
caacacctat aactgccagt gccctcctga
gtggacaggc cagttctgca cggaggacgt
ggatgagtgt cagctgcagc ccaacgcctg
ccacaatggg ggtacctgct tcaacacgct
gggtggccac agctgcgtgt gtgtcaatgg
ctggacaggc gagagctgca gtcagaatat
cgatgactgt gccacagccg tgtgcttcca
tggggccacc tgccatgacc gcgtggcttc
tttctactgt gcctgcccca tgggcaagac
tggcctcctg tgtcacctgg atgacgcctg
tgtcagcaac ccctgccacg aggatgctat
ctgtgacaca aatccggtga acggccgggc
catttgcacc tgtcctcccg gcttcacggg
tggggcatgt gaccaggatg tggacgagtg
ctctatcggc gccaaccccc tgcgagcactt
gggcaggtgc gtgaacacgc agggctcctt
cctgtgccag tgcggtcgtg gctacactgg
acctcgctgt gagaccgatg tcaacgagtg
tctgtcgggg ccctgccgaa accaggccac
gtgcctcgac cgcataggcc agttcacctg
tatctgtatg gcaggcttca caggaaccta
ttgcgaggtg gacattgacg agtgtcagag
tagcccctgt gtcaacggtg gggtctgcaa
ggaccgagtc aatggcttca gctgcacctg
cccctcgggc ttcagcggct ccacgtgtca
gctggacgtg gacgaatgcg ccagcacgcc
ctgcaggaat ggcgccaaat gcgtggacca
gcccgatggc tacgagtgcc gctgtgccga
gggctttgag ggcacgctgt gtgatcgcaa
cgtggacgac tgctcccctg acccatgcca
ccatggtcgc tgcgtggatg gcatcgccag
cttctcatgt gcctgtgctc ctggctacac
gggcacacgc tgcgagagcc aggtggacga
atgccgcagc agccctgcc gccatggcgg
caaatgccta gacctggtgg acaagtacct
ctgccgctgc cccttctgga ccacaggtgt
gaactgcgaa gtgaacattg acgactgtgc
cagcaacccc tgcacctttg gagtctgccg
tgatggcatc aaccgctacg actgtgtctg
```

-continued

```
ccaacctggc ttcacagggc cccttttgtaa
cgtggagatc aatgagtgtg cttccagccc
atgcggcgag ggaggttcct gtgtggatgg
ggaaaatggc ttccgctgcc tctgccgcc
tggctccttg cccccactct gcctccccc
gagccatccc tgtgcccatg agccctgcag
tcacggcatc tgctatgatg cacctggcgg
gttccgctgt gtgtgtgagc ctggctggag
tggccccgc tgcagccaga gcctggcccg
agacgcctgt gagtcccagc cgtgcaggc
cggtgggaca tgcagcagcg atggaatggg
tttccactgc acctgcccgc ctggtgtcca
gggacgtcag tgtgaactcc tctccccctg
cacccccgaac ccctgtgagc atggggccg
ctgcgagtct gccctgcc agctgcctgt
ctgctcctgc ccccagggct ggcaaggccc
acgatgccag caggatgtgg acgagtgtgc
tggccccgca ccctgtggcc ctcatggtat
ctgcaccaac ctggcaggga gtttcagctg
cacctgccat ggagggtaca ctggcccttc
ctgcgatcag gacatcaatg actgtgaccc
caacccatgc ctgaacggtg gctcgtgcca
agacggcgtg ggctccttt cctgctcctg
cctccctggt ttcgccggcc cacgatgcgc
ccgcgatgtg gatgagtgcc tgagcaaccc
ctgcggcccg ggcacctgta ccgaccacgt
ggcctccttc acctgcacct gcccgccagg
ctacggaggc ttccactgcg aacaggacct
gcccgactgc agcccagct cctgcttcaa
tggcgggacc tgtgtggacg gcgtgaactc
gttcagctgc ctgtgccgtc ccggctacac
aggagcccac tgccaacatg aggcagaccc
ctgcctctcg cggccctgcc tacacggggg
cgtctgcagc gccgcccacc ctggcttccg
ctgcacctgc ctcgagagct tcacgggccc
gcagtgccag acgctggtgg attggtgcag
ccgccagcct tgtcaaaacg ggggtcgctg
cgtccagact ggggcctatt gcctttgtcc
ccctgatgg agcggacgcc tctgtgacat
ccgaagcttg ccctgcaggg aggccgcagc
ccagatcggg gtgcggctgg agcagctgtg
```

-continued

```
tcaggcgggt gggcagtgtg tggatgaaga
cagctcccac tactgcgtgt gcccagaggg
ccgtactggt agccactgtg agcaggaggt
ggaccctgc ttggcccagc cctgccagca
tggggggacc tgccgtggct atatggggg
ctacatgtgt gagtgtcttc ctggctacaa
tggtgataac tgtgaggacg acgtggacga
gtgtgcctcc cagccctgcc agcacggggg
ttcatgcatt gacctcgtgg cccgctatct
ctgctcctgt cccccaggaa cgctggggt
gctctgcgag attaatgagg atgactgcgg
cccaggccca ccgctggact cagggccccg
gtgcctacac aatggcacct gcgtggacct
ggtgggtggt ttccgctgca cctgtccccc
aggatacact ggtttgcgct gcgaggcaga
catcaatgag tgtcgctcag gtgcctgcca
cgcggcacac acccgggact gcctgcagga
cccaggcgga ggtttccgtt gcctttgtca
tgctggcttc tcaggtcctc gctgtcagac
tgtcctgtct ccctgcgagt cccagccatg
ccagcatgga ggccagtgcc gtcctagccc
gggtcctggg ggtgggctga ccttcacctg
tcactgtgcc cagccgttct ggggtccgcg
ttgcgagcgg gtggcgcgct cctgccggga
gctgcagtgc ccggtgggcg tcccatgcca
gcagacgccc cgcgggccgc gctgcgcctg
ccccccaggg ttgtcggac cctcctgccg
cagcttcccg gggtcgccgc cggggggccag
caacgccagc tgcgcggccg ccccctgtct
ccacggggc tcctgccgcc ccgcgccgct
cgcgccctc ttccgctgcg cttgcgcgca
gggctggacc gggccgcgct gcgaggcgcc
cgccgcggca cccgaggtct cggaggagcc
gcggtgcccg cgcgccgcct gccaggccaa
gcgcggggac cagcgctgcg accgcgagtg
caacagccca ggctgcggct gggacggcgg
cgactgctcg ctgagcgtgg gcgacccctg
gcggcaatgc gaggcgctgc agtgctggcg
cctcttcaac aacagcgcgt gcgaccccgc
ctgcagctcg cccgcctgcc tctacgacaa
```

-continued

```
cttcgactgc cacgccggtg gccgcgagcg
cacttgcaac ccggtgtacg agaagtactg
cgccgaccac tttgccgacg gccgctgcga
ccagggctgc aacacggagg agtgcggctg
ggatgggctg gattgtgcca gcgaggtgcc
ggccctgctg gcccgcggcg tgctggtgct
cacagtgctg ctgccgccag aggagctact
gcgttccagc gccgactttc tgcagcggct
cagcgccatc ctgcgcacct cgctgcgctt
ccgcctggac gcgcacggcc aggccatggt
cttcccttac caccggccta gtcctggctc
cgaaccccgg gcccgtcggg agctggcccc
cgaggtgatc ggctcggtag taatgctgga
gattgacaac cggctctgcc tgcagtcgcc
tgagaatgat cactgcttcc ccgatgccca
gagcgccgct gactacctgg gagcgttgtc
agcggtggag cgcctggact tcccgtaccc
actgcgggac gtgcggggg agccgctgga
gcctccagaa cccagcgtcc cgctgctgcc
actgctagtg gcgggcgctg tcttgctgct
ggtcattctc gtcctgggtg tcatggtggc
ccggcgcaag cgcgagcaca gcaccctctg
gttccctgag ggcttctcac tgcacaagga
cgtggcctct ggtcacaagg gccggcggga
acccgtgggc caggacgcgc tgggcatgaa
gaacatggcc aagggtgaga gcctgatggg
ggaggtggcc acagactgga tggacacaga
gtgcccagag gccaagcggc taaaggtaga
ggagccaggc atgggggctg aggaggctgt
ggattgccgt cagtggactc aacaccatct
ggttgctgct gacatccgcg tggcaccagc
catggcactg acaccaccac agggcgacgc
agatgctgat ggcatggatg tcaatgtgcg
tggcccagat ggcttcaccc cgctaatgct
ggcttccttc tgtgggggg ctctggagcc
aatgccaact gaagaggatg aggcagatga
cacatcagct agcatcatct ccgacctgat
ctgccagggg gctcagcttg ggcacggac
tgaccgtact ggcgagactg ctttgcacct
ggctgccgt tatgcccgtg ctgatgcagc
caagcggctg ctggatgctg gggcagacac
```

```
caatgcccag gaccactcag gccgcactcc
cctgcacaca gctgtcacag ccgatgccca
gggtgtcttc cagattctca tccgaaaccg
ctctacagac ttggatgccc gcatggcaga
tggctcaacg gcactgatcc tggcggcccg
cctggcagta gagggcatgt ggaagagct
catcgccagc catgctgatg tcaatgctgt
ggatgagctt gggaaatcag ccttacactg
ggctgcggct gtgaacaacg tggaagccac
tttggccctg ctcaaaaatg gagccaataa
ggacatgcag gatagcaagg aggagacccc
cctattcctg gccgcccgcg agggcagcta
tgaggctgcc aagctgctgt tggaccactt
tgccaaccgt gagatcaccg accacctgga
caggctgccg cgggacgtag cccaggagag
actgcaccag acatcgtgc gcttgctgga
tcaacccagt gggccccgca gccccccgg
tccccacggc ctggggcctc tgctctgtcc
tccaggggcc ttcctccctg gcctcaaagc
ggcacagtcg gggtccaaga gagcaggag
gccccccggg aaggcggggc tggggccgca
ggggcccgg gggcggggca agaagctgac
gctggcctgc ccgggccccc tggctgacag
ctcggtcacg ctgtcgcccg tggactcgct
ggactccccg cggccttttcg gtgggcccc
tgcttcccct ggtggcttcc cccttgaggg
gccctatgca gctgccactg ccactgcagt
gtctctggca cagcttggtg gcccaggccg
ggcgggtcta gggcgccagc cccctggagg
atgtgtactc agcctgggcc tgctgaaccc
tgtggctgtg ccctcgatt gggcccggct
gccccacct gccccctccag gccctcgtt
cctgctgcca ctggcgccgg gaccccagct
gctcaaccca gggacccccg tctccccgca
ggagcggccc ccgccttacc tggcagtccc
aggacatggc gaggagtacc cggcggctgg
ggcacacagc agcccccaa aggcccgctt
cctgcgggtt cccagtgagc accccttacct
gacccatcc cccgaatccc ctgagcactg
ggccagcccc tcacctccct ccctctcaga
```

-continued
```
ctggtccgaa tccacgccta gcccagccac
tgccactggg gccatggcca ccaccactgg
ggcactgcct gcccagccac ttccttgtc
tgttcccagc tcccttgctc aggcccagac
ccagctgggg ccccagccgg aagttacccc
caagaggcaa gtgttggcct gagacgctcg
tcagttctta gatcttgggg gcctaaagag
accccgtcc tgcctcctt ctttctctgt
ctcttccttc cttttagtct ttttcatcct
cttctctttc caccaaccct cctgcatcct
tgccttgcag cgtgaccgag ataggtcatc
agcccaggc ttcagtcttc ctttatttat
aatgggtggg ggctaccacc caccctctca
gtcttgtgaa gagtctggga cctccttctt
ccccacttct ctcttcctc attcctttct
ctctccttct ggcctctcat ttccttacac
tctgacatga atgaattatt attatttta
ttttctttt tttttttaca ttttgtatag
aaacaaattc atttaaacaa acttattatt
attatttttt acaaaatata tatatggaga
tgctccctcc ccctgtgaac cccccagtgc
ccccgtgggg ctgagtctgt gggcccattc
ggccaagctg gattctgtgt acctagtaca
caggcatgac tgggatcccg tgtaccgagt
acacgaccca ggtatgtacc aagtaggcac
ccttgggcgc acccactggg gccaggggtc
gggggagtgt tgggagcctc ctccccaccc
cacctccctc acttcactgc attccagatg
ggacatgttc catagccttg ctggggaagg
gcccactgcc aactccctct gccccagccc
caccctttggc catctccctt tgggaactag
ggggctgctg gtgggaaatg ggagccaggg
cagatgtatg cattcctttg tgtccctgta
aatgtgggac tacaagaaga ggagctgcct
gagtggtact ttctcttcct ggtaatcctc
tggcccagcc tcatggcaga atagaggtat
ttttaggcta tttttgtaat atggcttctg
gtcaaaatcc ctgtgtagct gaattcccaa
gccctgcatt gtacagcccc ccactcccct
caccacctaa taaggaata gttaacactc
aaaaaaaaaa aaaaaaaa
```

The amino acid sequence encoded by NOTCH3 is SEQ ID NO:4, as follows:

```
MGPGARGRRR RRRPMSPPPP PPPVRALPLL LLLAGPGAAA
PPCLDGSPCA NGGRCTQLPS REAACLCPPG
WVGERCQLED PCHSGPCAGR GVCQSSVVAG TARFSCRCPR
GFRGPDCSLP DPCLSSPCAH GARCSVGPDG
RFLCSCPPGY QGRSCRSDVD ECRVGEPCRH GGTCLNTPGS
FRCQCPAGYT GPLCENPAVP CAPSPCRNGG
TCRQSGDLTY DCACLPGFEG QNCEVNVDDC PGHRCLNGGT
CVDGVNTYNC QCPPEWTGQF CTEDVDECQL
QPNACHNGGT CFNTLGGHSC VCVNGWTGES CSQNIDDCAT
AVCFHGATCH DRVASFYCAC PMGKTGLLCH
LDDACVSNPC HEDAICDTNP VNGRAICTCP PGFTGGACDQ
DVDECSIGAN PCEHLGRCVN TQGSFLCQCG
RGYTGPRCET DVNECLSGPC RNQATCLDRI GQFTCICMAG
FTGTYCEVDI DECQSSPCVN GGVCKDRVNG
FSCTCPSGFS GSTCQLDVDE CASTPCRNGA KCVDQPDGYE
CRCAEGFEGT LCDRNVDDCS PDPCHHGRCV
DGIASFSCAC APGYTGTRCE SQVDECRSQP CRHGGKCLDL
VDKYLCRCPS GTTGVNCEVN IDDCASNPCT
FGVCRDGINR YDCVCQPGFT GPLCNVEINE CASSPCGEGG
SCVDGENGFR CLCPPGSLPP LCLPPSHPCA
HEPCSHGICY DAPGGFRCVC EPGWSGPRCS QSLARDACES
QPCRAGGTCS SDGMGFHCTC PPGVQGRQCE
LLSPCTPNPC EHGGRCESAP GQLPVCSCPQ GWQGPRCQQD
VDECAGPAPC GPHGICTNLA GSFSCTCHGG
YTGPSCDQDI NDCDPNPCLN GGSCQDGVGS FSCSCLPGFA
GPRCARDVDE CLSNPCGPGT CTDHVASFTC
TCPPGYGGFH CEQDLPDCSP SSCFNGGTCV DGVNSFSCLC
RPGYTGAHCQ HEADPCLSRP CLHGGVCSAA
HPGFRCTCLE SFTGPQCQTL VDWCSRQPCQ NGGRCVQTGA
YCLCPPGWSG RLCDIRSLPC REAAAQIGVR
LEQLCQAGGQ CVDEDSSHYC VCPEGRTGSH CEQEVDPCLA
QPCQHGGTCR GYMGGYMCEC LPGYNGDNCE
DDVDECASQP CQHGGSCIDL VARYLCSCPP GTLGVLCEIN
EDDCGPGPPL DSGPRCLHNG TCVDLVGGFR
CTCPPGYTGL RCEADINECR SGACHAAHTR DCLQDPGGGF
RCLCHAGFSG PRCQTVLSPC ESQPCQHGGQ
CRPSPGPGGG LTFTCHCAQP FWGPRCERVA RSCRELQCPV
GVPCQQTPRG PRCACPPGLS GPSCRSFPGS
PPGASNASCA AAPCLHGGSC RPAPLAPFFR CACAQGWTGP
```

```
RCEAPAAAPE VSEEPRCPRA ACQAKRGDQR

CDRECNSPGC GWDGGDCSLS VGDPWRQCEA LQCWRLFNNS

RCDPACSSPA CLYDNFDCHA GGRERTCNPV

YEKYCADHFA DGRCDQGCNT EECGWDGLDC ASEVPALLAR

GVLVLTVLLP PEELLRSSAD FLQRLSAILR

TSLRFRLDAH GQAMVFPYHR PSPGSEPRAR RELAPEVIGS

VVMLEIDNRL CLQSPENDHC FPDAQSAADY

LGALSAVERL DFPYPLRDVR GEPLEPPEPS VPLLPLLVAG

AVLLLVILVL GVMVARRKRE HSTLWFPEGF

SLHKDVASGH KGRREPVGQD ALGMKNMAKG ESLMGEVATD

WMDTECPEAK RLKVEEPGMG AEEAVDCRQW

TQHHLVAADI RVAPAMALTP PQGDADADGM DVNVRGPDGF

TPLMLASFCG GALEPMPTEE DEADDTSASI

ISDLICQGAQ LGARTDRTGE TALHLAARYA RADAAKRLLD

AGADTNAQDH SGRTPLHTAV TADAQGVFQI

LIRNRSTDLD ARMADGSTAL ILAARLAVEG MVEELIASHA

DVNAVDELGK SALHWAAAVN NVEATLALLK

NGANKDMQDS KEETPLFLAA REGSYEAAKL LLDHFANREI

TDHLDRLPRD VAQERLHQDI VRLLDQPSGP

RSPPGPHGLG PLLCPPGAFL PGLKAAQSGS KKSRRPPGKA

GLGPQGPRGR GKKLTACPG PLADSSVTLS

PVDSLDSPRP FGGPPASPGG FPLEGPYAAA TATAVSLAQL

GGPGRAGLGR QPPGGCVLSL GLLNPVAVPL

DWARLPPPAP PGPSFLLPLA PGPQLLNPGT PVSPQERPPP

YLAVPGHGEE YPAAGAHSSP PKARFLRVPS

EHPYLTPSPE SPEHWASPSP PSLSDWSEST PSPATATGAM

ATTTGALPAQ PLPLSVPSSL AQAQTQLGPQ

PEVTPKRQVL A
```

Specific mutations in NOTCH3 which are indicative of having IM and/or being an autosomal dominant carrier of IM include an amino acid substitution at an amino acid residue corresponding to amino acid position 1519 of SEQ ID NO:4.

According to one embodiment, the amino acid substitution comprises a leucine to proline substitution at the amino acid position corresponding to Leu1519 of SEQ ID NO:4.

Detecting, in a sample, the presence or absence of one or more mutations in PDGFRB and/or NOTCH3 according to the methods of the present invention is carried out using various methods. In one embodiment, detecting involves sequencing at least a portion of a nucleic acid sequence in the sample corresponding to PDGFRB and/or NOTCH3 (i.e., SEQ ID NO:1 and SEQ ID NO:3, respectively). For example, detecting can be carried out by direct sequencing of the PDGFRB and/or NOTCH3 genes, or regions of PDGFRB and/or NOTCH3 comprising the one or more mutations identified herein.

Direct sequencing assays typically involve isolating DNA sample from a subject using any suitable method known in the art, and cloning the region of interest to be sequenced into a suitable vector for amplification by growth in a host cell (e.g., bacteria) or direct amplification by PCR or other amplification assay. Following amplification, the DNA can be sequenced using any suitable method. One suitable method involves high-throughput next generation sequencing ("NGS") to identify genetic variation. Various NGS sequencing chemistries are available and suitable for use in carrying out the methods of the present invention, including pyrosequencing (Roche® 454), sequencing by reversible dye terminators (Illumina® HiSeq, Genome Analyzer and MiSeq systems), sequencing by sequential ligation of oligonucleotide probes (Life Technologies® SOLiD), and hydrogen ion semiconductor sequencing (Life Technologies®, Ion Torrent™). Alternatively, classic sequencing methods, such as the Sanger chain termination method or Maxam-Gilbert sequencing can be used to carry out the methods of the present invention.

In another embodiment, detecting, in a sample, the presence or absence of one or more mutations in PDGFRB and/or NOTCH3 according to the methods of the present invention is carried out with a hybridization assay. This involves using one or more oligonucleotide probes having a nucleotide sequence that is complementary to a nucleotide sequence of a nucleic acid molecule in a sample comprising the one or more mutations in PDGFRB and/or NOTCH3. The oligonucleotide probes are designed to be complementary to the wildtype, non-mutant nucleotide sequence and/or the mutant nucleotide sequence of PDGFRB and/or NOTCH3 to effectuate the detection of the presence or the absence of the mutation in the sample from the subject upon contacting the sample with the oligonucleotide probes. A variety of hybridization assays that are known in the art are suitable for use in this embodiment. For example, and without limitation, the following methods may be used: direct hybridization assays, such as northern blot or Southern blot (see e.g., Ausabel et al., Current Protocols in Molecular Biology, John Wiley & Sons, NY (1991), which is hereby incorporated by reference in its entirety). Alternatively, direct hybridization can be carried out using an array based method where a series of oligonucleotide probes designed to be complementary to a particular non-mutant or mutant gene region are affixed to a solid support. The DNA sample from the subject is contacted with the array containing the oligonucleotide probes, and hybridization of nucleic acid molecules from the sample to their complementary oligonucleotide probes on the array surface is detected. Examples of direct hybridization array platforms include, without limitation, the Affymetrix GeneChip or SNP arrays and Illumina's Bead Array.

Other common genotyping methods include, but are not limited to, restriction fragment length polymorphism assays; amplification based assays, such as molecular beacon assays; nucleic acid arrays; allele-specific PCR; primer extension assays, such as allele-specific primer extension (e.g., Illumina® Infinium® assay), arrayed primer extension (see Krjutskov et al., "Development of a Single Tube 640-ples Genotyping Method for Detection of Nucleic Acid Variations on Microarrays," *Nucleic Acids Res.* 36(12) e75 (2008), which is hereby incorporated by reference in its entirety); homogeneous primer extension assays; primer extension with detection by mass spectrometry (e.g., Sequenomx iPLEX SNP genotyping assay) (see Zheng et al., "Cumulative Association of Five Genetic Variants with Prostate Cancer," *N. Eng. J. Med.* 358(9):910-919 (2008), which is hereby incorporated by reference in its entirety); multiplex primer extension sorted on genetic arrays; flap endonuclease assays (e.g., the Invader® assay) (see Olivier M., "The Invader Assay for SNP Genotyping," *Mutat. Res.* 573:103-110 (2005), which is hereby incorporated by reference in its entirety); 5' nuclease assays, such as the TaqMan® assay (see U.S. Pat. No. 5,210,015 to Gelfand et al. and U.S. Pat. No. 5,538,848 to Livak et al., both of which are hereby incorporated by reference in their entirety); oligonucleotide ligation assays, such as ligation with rolling circle amplification, homogeneous ligation, OLA (see U.S. Pat. No. 4,988,617 to Landgren et al., which is hereby incorporated by reference in its entirety), and multiplex ligation reactions followed by PCR where zipcodes are incorporated into ligation reaction probes and amplified PCR products are determined by electrophoretic or universal zipcode array readout (see U.S. Pat. No. 7,429,453 and U.S. Pat. No. 7,312,039 to Barany et al., both of which are hereby incorporated by reference in their entirety). Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection.

Detecting, in the sample, the presence or absence of the one or more mutations in PDGFRB and/or NOTCH3 indicates the subject has a mutation that causes infantile myofibromatosis. Accordingly, the subject is diagnosed as having and/or being a carrier for infantile myofibromatosis based on said detecting in the sample.

In carrying out the methods of the present invention, a "subject" includes any animal including, without limitation, mammalian subjects such as humans, non-human primates, dogs, cats, rodents, horses, cattle, sheep, and pigs. In one embodiment, the subject is a human subject.

In one embodiment, the diagnostic method of the present invention is carried out for prenatal or neonatal testing, or to test embryos as carriers of infantile myofibromatosis.

A subject diagnosed as having infantile myofibromatosis pursuant to the method of the present invention may be administered a therapy suitable for treatment of infantile myofibromatosis. Suitable therapies may include, for example and without limitation, removal of a tumor, administering radiation therapy, administering chemotherapy, and/or modulating PDGFRB and/or NOTCH3 gene expression and/or PDGFRB and/or NOTCH3 encoded protein activity.

Another aspect of the present invention relates to a method of treating a subject having infantile myofibromatosis. This method involves selecting a subject having one or more mutations in PDGFRB and/or NOTCH3 and administering a therapy suitable for treating infantile myofibromatosis to the selected subject.

Particular mutations in PDGFRB and/or NOTCH3 and methods of detecting these mutations are described supra.

In one embodiment, the subject is undergoing treatment for infantile myofibromatosis at the time the one or more mutations in PDGFRB and/or NOTCH3 is detected. Following detection of the one or more mutations, the subject's therapy is modified to implement a more precise treatment that is suitable for treating infantile myofibromatosis. In another embodiment, the subject is not undergoing treatment for infantile myofibromatosis at the time the one or more mutations is detected, i.e., the gene mutation(s) are detected at the time of diagnosis. In accordance with this embodiment, a preferable course of treatment is determined based on the diagnosis.

As discussed supra, suitable therapies that may be administered according to this aspect of the present invention include, for example and without limitation, removal of a tumor, administering radiation therapy, administering chemotherapy, and/or modulating PDGFRB and/or NOTCH3 gene expression and/or PDGFRB and/or NOTCH3 encoded protein activity.

A further aspect of the present invention relates to a method of preventing or treating symptoms associated with infantile myofibromatosis. This method involves selecting a subject having one or more mutations in PDGFRB and/or NOTCH3 and administering to the selected subject an agent that modulates PDGFRB and/or NOTCH3 gene expression and/or PDGFRB and/or NOTCH3 encoded protein activity under conditions effective to prevent or treat symptoms associated with infantile myofibromatosis in the subject.

In one embodiment, the selected subject is administered an agent that modulates PDGFRB gene expression and/or PDGFRB encoded protein activity. Agents that are known to modulate PDGFRB gene expression and/or PDGFRB encoded protein activity include, without limitation, GLEEVEC® (imatinib mesylate) (see Gibbs et al., "Decoupling of Tumor-initiating Activity from Stable Immunophenotype in HoxA9-Meis1-driven AML," *Cell Stem Cell.* 10:210-217 (2012); Huang et al., "Glucosylceramide Synthase Inhibitor PDMP Sensitizes Chronic Myeloid Leukemia T315I Mutant to Bcr-AbI Inhibitor and Cooperatively Induces Glycogen Synthase Kinase-3-regulated Apoptosis," *FASEB J.* 25:3661-3673 (2011); and Yamakawa et al., "Pharmacokinetic Impact of SLCO1A2 Polymorphisms on Imatinib Disposition in Patients with Chronic Myeloid Leukemia," *Clin. Pharmacol. Ther.* 90:157-163 (2011), which are hereby incorporated by reference in its entirety); imatinib mesylate (see Griaud et al., "A Pathway from leukemogenic Oncogenes and Stem Cell Chemokines to RNA Processing via THOC5," *Leukemia* 27:932-940 (2013); Huang et al., "Glucosylceramide Synthase Inhibitor PDMP Sensitizes Chronic Myeloid Leukemia T315I Mutant to Bcr-AbI Inhibitor and Cooperatively Induces Glycogen Synthase Kinase-3-regulated Apoptosis," *FASEB J.* 25:3661-3673 (2011); and Todd et al., "The MAPK Pathway Functions as a Redundant Survival Signal that Reinforces the PI3K Cascade in c-Kit Mutant Melanoma," *Oncogene Epub ahead of print* (2012), which are hereby incorporated by reference in its entirety); Sorafenib (Nexavar) (see Segarra et al., "Semaphorin 6A Regulates Angiogenesis by Modulating VEGF Signaling," *Blood* 120:4104-4115 (2012); Shao et al., "BH3-only Protein Silencing Contributes to Acquired Resistance to PLX4720 in Human Melanoma," *Cell Death Differ.* 19:2029-2039 (2012); and Nicolaides et al., "Targeted Therapy for BRAFV600E Malignant Astrocytoma," *Clin. Cancer Res.* 17:7595-7604 (2011), which are hereby incorporated by reference in their entirety); Sunitinib Malate (Sutent) (see Riddell et al., "Peroxiredoxin 1 Controls Prostate Cancer Growth through Toll-like Receptor 4-dependent Regulation of Tumor Vasculature," *Cancer Res.* 71:1637-1646 (2011); van Rooijen et al., "von Hippel-lindau Tumor Suppressor Mutants Faithfully Model Pathological Hypoxia-driven Angiogenesis and Vascular Retinopathies in Zebrafish," *Dis. Model Mech.* 3:343-353 (2010); and Lin et al., "Autophagic Activation Potentiates the Antiproliferative Effects of Tyrosine Kinase Inhibitors in Medullary Thyroid Cancer," *Surgery* 152:1142-1149 (2012), which are hereby incorporated by reference in their entirety); Ponatinib (AP24534) (see Bicocca et al., "Crosstalk Between ROR1 and the Pre-B Cell Receptor Promotes Survival of t(1;19) Acute Lymphoblastic Leukemia," *Cancer Cell* 22:656-667 (2012) and Melkus et al., "Biological Effects of T315I-mutated BCR-ABL in an Embryonic Stem Cell-derived Hematopoiesis Model," *Exp. Hematol.* 41:335-345 (2013), which are hereby incorporated by reference in its entirety); BIBF1120 (Vargatef) (see Chen et al., "PDGF Signalling Controls Age-dependent Proliferation in Pancreatic (3-cells," *Nature* 478:349-355 (2011); Harr et al., "Inhibition of Lck Enhances Glucocorticoid Sensitivity and Apoptosis in Lymphoid Cell Lines and in Chronic Lymphocytic Leukemia," *Cell Death Differ.* 17:1381-1391 (2010), which are hereby incorporated by reference in their entirety); Axitinib (see Martin et al., "Metformin Accelerates the Growth of BRAF$^{V600E}$-driven Melanoma by Upregulating VEGF-A," *Cancer Discov.* 2:344-355 (2012); Wuestefeld et al., "Impact of VEGF on Astrocytes: Analysis of Gap Junctional Intercellular Communication, Proliferation, and Motility," *Glia.* 60:936-947 (2012); and Wang et al., "Axitinib Targeted Cancer Stemlike Cells to Enhance Efficacy of Chemotherapeutic Drugs via Inhibiting the Drug Transport Function of ABCG2," *Mol. Med.* 18:887-898 (2012), which are hereby incorporated by reference in its entirety); Crenolanib (CP-868596); Covitinib (TKI-258) (see Wasag et al., "The Kinase Inhibitor TKI258 is Active Against the Novel CUX1-FGFR1 Fusion Detected in a Patient with T-lymphoblastic Leukemia/Lymphoma and t(7;8)(q22; p11)," *Haematologica* 96:922-926 (2011); Gozgit et al., "Ponatinib (AP24534), a Multatargeted Pan-FGFR Inhibitor with Activity in Multiple FGFR-amplified or Mutated Cancer Models," *Mol. Cancer Ther.* 11:690-699 (2012); and Lamont et al., "Small Molecule FGF Receptor Inhibitors Block FGFR-dependent Urothelial Carcinoma Growth In Vitro and In Vivo," *Br. J. Cancer* 104:75-82 (2011), which are hereby incorporated by reference in their entirety); Tivozanib (AV-951); TSU-68 (SU 6668) (see Trzcinska-Daneluti et al., "Use of Kinase Inhibitors to Correct ΔF508-CFTR Function," *Mol. Cell Proteomics* 11:745-757 (2012) and Jin et al., "Positron Emission Tomography Imaging of Tumor Angiogenesis and Monitoring of Antiangiogenic Efficacy Using the Novel Tetrameric Peptide Probe (64Cu-cyclam-RAFT-c-(-RGDfK-)4," *Angiogenesis* 15:569-580 (2012), which are hereby incorporated by reference in its entirety); Masitinib (AB1010); CP673451; Linifanib (ABT-869) (see Zhong et al., "TSLP Signaling Network Revealed by SILAC-based Phosphoproteomics," *Mol. Cell Proteomics* 11:M112.017764 (2012) and Fingas et al., "Targeting PDGFR-β in Cholangiocarcinoma," *Liver Int.* 32:400-409 (2012), which are hereby incorporated by reference in their entirety); Amuvatinib (MP-470) (see Zhang et al., "Activation of the AXL Kinase Causes Resistance to EGFR-targeted Therapy in Lung Cancer," *Nat. Genet.* 44:852-860 (2012), which is hereby incorporated by reference in its entirety); MK-2461; Motesanib Diphosphate (AMG-706) (see Tang et al., "VEGF/SDF-1 Promotes Cardiac Stem Cell Mobilization and Myocardial Repair in the Infarcted Heart," *Cariovasc. Res.* 91:401-411 (2011), which is hereby incorporated by reference in its entirety); Pazopanib; Dovitinib Dilactic acid (TKI258 Dilactic acid) (see Wasag et al., "The Kinase Inhibitor TKI258 is Active Against the Novel CUX1-FGFR1 Fusion Detected in a Patient with T-lymphoblastic Leukemia/Lymphoma and t(7;8)(q22;p11)," *Haematologica* 96:922-926 (2011); Gozgit et al., "Ponatinib (AP24534), a Multitargeted Pan-FGFR Inhibitor with Activity in Multiple FGFR-amplified or Mutated Cancer Models," *Mol. Cancer Ther.* 11:690-699 (2012); and Lamont et al., "Small Molecule FGF Receptor Inhibitors Block FGFR-dependent Urothelial Carcinoma Growth In Vitro and In Vivo," *Br. J. Cancer* 104:75-82 (2011), which are hereby incorporated by reference in their entirety); Ki8751 (see Hamerlik et al., "Autocrine VEGF-VEGFR2-neuropilin-1 Signaling Promotes Glioma Stem-like Cell Viability and Tumor Growth," *J. Exp. Med.* 209:507-520 (2012) and Trzcinska-Daneluti et al., "Use of Kinase Inhibitors to Correct ΔF508-CFTR Function," *Mol. Cell Proteomics* 11:745-757 (2012), which are hereby incorporated by reference in their entirety); Telatinib (BAY 57-9352); PP-121; KRN 633; Tyrphostin AG 1296 (AG1296); Pazopanib HCL (see Gorbunova et al., "VEGFR2 and Src Kinase Inhibitors Suppress Andes Virus-induced Endothelial Cell Permeability," *J. Virol.* 85:2296-2303 (2011), which is hereby incorporated by reference in its entirety); Tarceva® (erlotinib hydrochloride); TASIGNA® (nilotinib); urea derivatives as described in U.S. Patent Application Serial No. 2005/0197371 to Milanov et al., which is hereby incorporated by reference in its entirety; SU101 (see Shawver et al., "Inhibition of Platelet-derived Growth Factor-mediated Signal Transduction and Tumor Growth by N-[4-(trifluoromethyl)-phenyl]5-methylisoxazole-4-carboxamide," *Clin. Cancer Res.* 3:1167-1177 (1997), which is hereby incorporated by reference in its entirety); SU11657 (see Cain et al., "Complete Remission of TEL-PDGFRB-induced Myeloproliferative Disease in Mice by Receptor Tyrosine Kinase Inhibitor SU11657," *Blood* 104:561-564 (2004), which is hereby incorporated by reference in its entirety); CT52923 (see Lokker et al., "Platelet-derived Growth Factor (PDGF) Autocrine Signaling Regulates Survival and Mitogenic Pathways in Glioblastoma Cells: Evidence that the Novel PDGF-C and PDGF-D Ligands May Play a Role in the Development of Brain Tumors," *Cancer Res.* 62:3729-3735 (2002), which is hereby incorporated by reference in its entirety); quinoline ether inhibitors (see Plé et al., "Discovery of New Quinoline Ether Inhibitors with High Affinity and Selectivity for PDGFR Tyrosine Kinases," *Bioorganic & Med. Chem. Lett.* 22:3050-3055 (2012), which is hereby incorporated by reference in its entirety); AZD2932 (see Plé et al., "Discovery of AZD2932, a New Quinazoline Ether Inhibitor with High Affinity for VEGFR-2 and PDGRF Tyrosine Kinases," *Bioorganic & Med. Chem. Lett.* 22:262-266 (2012), which is hereby incorporated by reference in its entirety); AC710 (see Liu et al., "Discovery of AC710, a Globally Selective Inhibitor of Platelet-derived Growth Factor Receptor-family Kinases," *ACS Med. Chem. Lett.* 3:997-1002 (2012), which is hereby incorporated by reference in its entirety); benzimidazole derivatives (see Li et al., "Discovery of Benzimidazole Derivatives as Novel Multi-target EGFR, VEGRF-2 and PDGFR Kinase Inhibitors," *Bioorganic & Med. Chem.* 19:4529-4535 (2011), which is hereby incorporated by reference in its entirety); 2-amino-4-m-bromoanilino-6-arylmethyl-7H-pyrrolo[2,3-d]pyrimidines (see Gangjee et al., "Design, Synthesis and Evaluation of 2-amino-4-m-bromoanilino-6-arylmethyl-7H-pyrrolo[2,3-d]pyrimidines as Tyrosine Kinase Inhibitors and Antiangiogenic Agents," *Bioorganic & Med. Chem.* 18:5261-5273 (2010), which is hereby incorporated by reference in its entirety); aminopyrazolopyridine ureas (see Dai et al., "Identification of Aminopyrazolopyridine Ureas as Potent VEGFR/PDFR Multitargeted Kinase Inhibitors," *Bioorganic & Med. Chem. Lett.* 18:386-390 (2008), which is hereby incorporated by reference in its entirety); bis(benzo[b]furan-2-yl)methanones (see Mahboobi et al., "Inhibition of FLT3 and PDGFR Tyrosine Kinase Activity by Bis(benzo[b]furan-2-yl)methanones," *Bioorganic & Med. Chem.* 15:2187-2197 (2007), which is hereby incorporated by reference in its entirety); 7-[3-(cyclohexylmethyl)ureido]-3-{1-methyl-1H-pyrrolo[2,3,-b]pyridine-3-yl}quinoxalin-2(1H)-one derivatives (see Aoki et al., "Potent Platelet-derived Growth Factor-β Receptor (PDGF-βR) Inhibitors: Synthesis and Structure-activity Relationships of 7-[3-(cyclohexylmethyl)ureido]-3-{1-methyl-1H-pyrrolo[2,3,-b]pyridine-3-yl}quinoxalin-2(1H)-one Derivatives," *Chem. & Pharm. Bull.* 55:255-267 (2007), which is hereby incorporated by reference in its entirety); RO4383596 (see McDermott et al., "RO4383596, an Orally Active KDR, FGFR, and PDGFR Inhibitor: Synthesis and Biological Evaluation," *Bioorganic and Med. Chem.* 13:4835-4841 (2005), which is hereby incorporated by reference in its entirety); tricyclic amine derivatives as described in PCT Publication No. WO 2008/078100 to Berdini et al., which is hereby incorporated by reference in its entirety; benzylbenzimidazolyl derivatives as described in U.S. Patent Application Publication No. 2007/0066606 to Stahle et al., which is hereby incorporated by reference in its entirety; amides as described in PCT Publication No. WO 2010/096395 to Chen, which is hereby incorporated by reference in its entirety; fused heterocyclic derivatives as described in U.S. Patent Application Publication No. 2010/0168424 to Sakai et al., which is hereby incorporated by reference in its entirety; imidazopyridazine derivatives as described in U.S. Pat. No. 8,034,812 to Sakai et al., which is hereby incorporated by reference in its entirety; and PDGFRB modulators as described in PCT Publication No. WO 2004/020583 to Turaga, which is hereby incorporated by reference in its entirety.

In another embodiment, the selected subject is administered an agent that modulates NOTCH3 gene expression and/or NOTCH3 encoded protein activity. Agents that are known to modulate NOTCH3 gene expression and/or NOTCH3 encoded protein activity include, without limitation, Semagacestat (LY450139) (see Borgegard et al., "First and Second Generation γ-secretase Modulators (GSMs) Modulate Amyloid-β (Aβ) Peptide Production through Different Mechanisms," *J. Biol. Chem.* 287:11810-11819 (2012), which is hereby incorporated by reference in its entirety); YO-01027; anti-NRR1 and anti-NRR2 antibodies (see Wu et al., "Therapeutic Antibody Targeting of Individual Notch Receptors," *Nature* 464:1052-1059 (2010), which is hereby incorporated by reference in its entirety), and the γ-secretase inhibitor MRK-003 (see Konishi et al., "γ-Secretase Inhibitor Prevents Notch3 Activation and Reduces Proliferation in Human Lung Cancers," *Cancer Res* 67:8051-8057 (2007), which is hereby incorporated by reference in its entirety).

In a further embodiment, the selected subject is administered an agent that modulates both PDGFRB and NOTCH3 gene expression and/or PDGFRB and NOTCH3 encoded protein activity.

In one embodiment of carrying out this method of the present invention, symptoms associated with infantile myofibromatosis are prevented in the selected subject. In another embodiment of the present invention, symptoms associated with infantile myofibromatosis are treated in the selected subject.

In one embodiment, the agent administered to the subject modulates mutant PDGFRB and/or NOTCH3 gene expression and/or mutant PDGFRB and/or NOTCH3 encoded protein activity. Mutations associated with infantile myofibromatosis include those described supra.

In carrying out this method, one or more anti-infantile myofibromatosis therapies are administered to the selected subject in conjunction with administering the agent that modulates PDGFRB and/or NOTCH3 gene expression and/or PDGFRB and/or NOTCH3 encoded protein activity. Suitable anti-infantile myofibromatosis therapies are described supra.

Suitable inhibitors of PDGFRB and/or NOTCH3 gene expression include nucleic acid inhibitors of PDGFRB and/or NOTCH3 gene expression, such as e.g., siRNA, shRNA, antisense molecules, microRNAs, etc. The use of antisense methods to inhibit the in vivo translation of genes and subsequent protein expression is well known in the art (see e.g., U.S. Pat. No. 7,425,544 to Dobie et al.; U.S. Pat. No. 7,307,069 to Karras et al.; U.S. Pat. No. 7,288,530 to Bennett et al.; and U.S. Pat. No. 7,179,796 to Cowsert et al., all of which are hereby incorporated by reference in their entirety). Antisense nucleic acids are nucleic acid molecules (e.g., molecules containing DNA nucleotides, RNA nucleotides, or modifications (e.g., modifications that increase the stability of the molecule, such as 2'-O-alkyl (e.g., methyl) substituted nucleotides) or combinations thereof that are complementary to, or that hybridize to, at least a portion of a specific nucleic acid molecule, such as an mRNA molecule (see e.g., Weintraub, "Antisense DNA and RNA," *Scientific Am.* 262:40-46 (1990), which is hereby incorporated by reference in its entirety). The antisense nucleic acid molecule hybridizes to its corresponding target nucleic acid molecule to form a double-stranded molecule which interferes with translation of the mRNA, as the cell will not translate a double-stranded mRNA. Antisense nucleic acids suitable for use in the methods of the present invention are typically at least 10-12 nucleotides in length or, for example, at least 15, 20, 25, 50, 75, or 100 nucleotides in length. The antisense nucleic acid can also be as long as the target nucleic acid with which it is intended to form an inhibitory duplex. Antisense nucleic acids can be introduced into cells as antisense oligonucleotides, or can be produced in a cell in which a nucleic acid encoding the antisense nucleic acid has been introduced, for example, using gene therapy methods.

siRNAs are double stranded synthetic RNA molecules approximately 20-25 nucleotides in length with short 2-3 nucleotide 3' overhangs on both ends. The double stranded siRNA molecule represents the sense and anti-sense strand of a portion of the mRNA molecule (i.e., SEQ ID NO:1 and/or SEQ ID NO:3). siRNA molecules are typically designed to target a region of the mRNA target approximately 50-100 nucleotides downstream from the start codon. Upon introduction into a cell, the siRNA complex triggers the endogenous RNA interference (RNAi) pathway, resulting in the cleavage and degradation of the target mRNA molecule.

Various improvements of siRNA compositions, such as the incorporation of modified nucleosides or motifs into one or both strands of the siRNA molecule to enhance stability, specificity, and efficacy, have been described and are suitable for use in accordance with this aspect of the present invention (see e.g., PCT Patent Application Publication WO 2004/015107 to Giese et al.; PCT Patent Application Publication WO 2003/070918 to McSwiggen et al.; PCT Patent Application Publication WO 1998/39352 to Imanishi et al.; U.S. Patent Application Publication No. 2002/0068708 to Jesper et al.; U.S. Patent Application Publication No. 2002/0147332 to Kaneko et al; and U.S. Patent Application Publication No. 2008/0119427 to Bhat et al., all of which are hereby incorporated by reference in their entirety).

Short or small hairpin RNA molecules are similar to siRNA molecules in function, but comprise longer RNA sequences that make a tight hairpin turn. shRNA is cleaved by cellular machinery into siRNA and gene expression is silenced via the cellular RNA interference pathway.

In accordance with the methods of the present invention, the mode of administering therapeutic agents, including the use of suitable delivery vehicles, to a subject will vary depending on the type of therapeutic agent (e.g., nucleic acid molecule, ribonucleoside analogue, or small molecule). For example, ribonucleoside analogues and small molecule inhibitors can be administered directly, preferably systemically. In contrast, inhibitory nucleic acid molecules (i.e., antisense, siRNA, etc.), may be incorporated into a gene therapy vector to facilitate delivery. Suitable gene therapy vectors include, without limitation, adenovirus, adeno-associated virus, retrovirus, lentivirus, or herpes virus.

Adenoviral viral vector gene delivery vehicles can be readily prepared and utilized as described in Berkner, "Development of Adenovirus Vectors for the Expression of Heterologous Genes," *Biotechniques* 6:616-627 (1988); Rosenfeld et al., "Adenovirus-Mediated Transfer of a Recombinant Alpha 1-Antitrypsin Gene to the Lung Epithelium In Vivo," *Science* 252:431-434 (1991); PCT Patent Application Publication WO 93/07283 to Curiel et al.; PCT Patent Application Publication WO 93/06223 to Perricaudet et al.; and PCT Patent Application Publication WO 93/07282 to Curiel et al., all of which are hereby incorporated by reference in their entirety.

Adeno-associated viral vector vehicles can be constructed and used to deliver inhibitory nucleic acid molecules as described by Chatterjee et al., "Dual-Target Inhibition of HIV-1 In Vitro by Means of an Adeno-associated Virus Antisense Vector," *Science* 258:1485-1488 (1992); Ponnazhagan et al., "Suppression of Human Alpha-globin Gene Expression Mediated by the Recombinant Adeno-associated Virus 2-based Antisense Vectors," *J. Exp. Med.* 179:733-738 (1994); and Zhou et al., "Adeno-Associated Virus 2-mediated Transduction and Erythroid Cell-specific Expression of a Human Beta-globin Gene," *Gene Ther.* 3:223-229 (1996), all of which are hereby incorporated by reference in their entirety. In vivo use of these vehicles is described in Flotte et al., "Stable In Vivo Expression of the Cystic Fibrosis Transmembrane Conductance Regulator With an Adeno-associated Virus Vector," *Proc. Nat'l. Acad. Sci.* 90:10613-10617 (1993) and Kaplitt et al., "Long-Term Gene Expression and Phenotypic Correction Using Adeno-associated Virus Vectors in the Mammalian Brain," *Nature Genet.* 8:148-153 (1994), both of which are hereby incorporated by reference in their entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, all of which are hereby incorporated by reference in their entirety.

Retroviral vectors which have been modified to form infective transformation systems can also be used to deliver inhibitory nucleic acid molecules to a target cell. One such type of retroviral vector is disclosed in U.S. Pat. No. 5,849,586 to Kriegler et al., which is hereby incorporated by reference in its entirety.

Gene therapy vectors carrying the therapeutic nucleic acid molecule are administered to a subject by, for example, intravenous injection or local administration (see e.g., U.S. Pat. No. 5,328,470 to Nabel et al., which is hereby incorporated by reference in its entirety). The pharmaceutical preparation of the vector can include the vector in an acceptable diluent, or can comprise a slow release matrix in which the vector delivery vehicle is imbedded. Alternatively, where the complete delivery vector can be produced intact from recombinant cells, e.g., retroviral vectors, the pharmaceutical preparation can include one or more cells which produce the gene delivery system.

The therapeutic agents of the present invention (i.e., PDGFRB and/or NOTCH3 gene expression modulating agents and or PDGFRB and/or NOTCH3 encoded protein modulating agents) can be administered via any standard route of administration known in the art, including, but not limited to, parenteral (e.g., intravenous, intraarterial, intramuscular, subcutaneous injection, intrathecal), oral (e.g., dietary), topical, transmucosal, or by inhalation (e.g., intrabronchial, intranasal or oral inhalation, or intranasal drops). Typically, parenteral administration is a preferred mode of administration.

Therapeutic agents of the present invention are formulated in accordance with their mode of administration. For oral administration, for example, the therapeutic agents are formulated into an inert diluent or an assimilable edible carrier, enclosed in hard or soft shell capsules, compressed into tablets, or incorporated directly into food. Agents of the present invention may also be administered in a time release manner incorporated within such devices as time-release capsules or nanotubes. Such devices afford flexibility relative to time and dosage. For oral therapeutic administration, the agents of the present invention may be incorporated with excipients and used in the form of tablets, capsules, elixirs, suspensions, syrups, and the like. Such compositions and preparations should contain at least 0.1% of the agent, although lower concentrations may be effective and indeed optimal. The percentage of the agent in these compositions may, of course, be varied and may conveniently be between about 2% to about 60% of the weight of the unit. The amount of an agent of the present invention in such therapeutically useful compositions is such that a suitable dosage will be obtained.

Also specifically contemplated are oral dosage forms of the therapeutic agents. The agents may be chemically modified so that oral delivery of the derivative is efficacious. Generally, the chemical modification contemplated is the attachment of at least one moiety to the component molecule itself, where said moiety permits inhibition of proteolysis and uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline (see Abuchowski and Davis, "Soluble Polymer-enzyme Adducts," In *Enzymes as Drugs*, Hocenberg and Roberts, eds., Wiley-Interscience (1981), which is hereby incorporated by reference in their entirety). Other polymers that could be used are poly-1,3-dioxolane and poly-1,3,6-tioxocane. Preferred for pharmaceutical usage are polyethylene glycol moieties.

The therapeutic agents may also be delivered systemically, formulated for parenteral administration by injection, e.g., by bolus injection or continuous infusion. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. In all cases, the form must be sterile and must be fluid to the extent that easy syringability exists. It must be stable under the conditions of manufacture and storage and must be preserved against the contaminating action of microorganisms, such as bacteria and fungi.

Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing, and/or dispersing agents.

Intraperitoneal or intrathecal administration of the therapeutic agents can also be achieved using infusion pump devices such as those described by Medtronic (Northridge, Calif.). Such devices allow continuous infusion of desired compounds avoiding multiple injections and multiple manipulations.

In addition to the formulations described previously, the agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

Effective doses of the therapeutic agents will vary depending upon many different factors, including type and stage of tumor, mode of administration, target site, physiological state of the patient, other medications or therapies administered, and physical state of the patient relative to other medical complications. Treatment dosages need to be titrated to optimize safety and efficacy.

A further aspect of the present invention involves diagnosing a subject as having or being a carrier for infantile myofibromatosis based on detected levels of PDGFRB and/or NOTCH3 gene expression and/or PDGFRB and/or NOTCH3 encoded protein levels and/or activity in a subject. This method involves providing an isolated biological sample from a subject; contacting the sample with one or more reagents suitable for detecting PDGFRB and/or NOTCH3 RNA and/or protein levels; detecting, in the sample, levels of PDGFRB and/or NOTCH3 RNA and/or protein based on said contacting; and diagnosing the subject as having and/or being a carrier for infantile myofibromatosis based on said detecting, where decreased levels of PDGFRB and/or NOTCH3 RNA and/or protein compared to normal levels of PDGFRB and/or NOTCH3 RNA and/or protein indicates the subject has or is a carrier for infantile myofibromatosis.

In another aspect, the present invention relates to a treatment method which involves selecting a subject having levels of PDGFRB and/or NOTCH3 gene expression and/or PDGFRB and/or NOTCH3 encoded protein levels and/or activity at a higher or lower than normal level and administering a therapy suitable for treating infantile myofibromatosis to the subject. According to one embodiment, this method involves selecting a subject having decreased levels of PDGFRB and/or NOTCH3 RNA and/or protein compared to a subject having normal levels of PDGFRB and/or NOTCH3 RNA and/or protein and administering a therapy suitable for treating infantile myofibromatosis to the selected subject.

In yet a further aspect, the present invention relates to preventing or treating symptoms associated with infantile myofibromatosis. This method involves selecting a subject having levels of PDGFRB and/or NOTCH3 gene expression and/or PDGFRB and/or NOTCH3 encoded protein levels and/or activity at a higher or lower than normal level and administering to the selected subject an agent that modulates PDGFRB and/or NOTCH3 gene expression and/or PDGFRB and/or NOTCH3 encoded protein levels and/or activity under conditions effective to prevent or treat symptoms associated with infantile myofibromatosis in the subject. According to one embodiment, this method involves selecting a subject having decreased levels of PDGFRB and/or NOTCH3 RNA and/or protein compared to a subject having normal levels of PDGFRB and/or NOTCH3 RNA and/or protein and administering to the selected subject an agent that modulates PDGFRB and/or NOTCH3 gene expression and/or PDGFRB and/or NOTCH3 encoded protein activity under conditions effective to prevent or treat symptoms associated with infantile myofibromatosis in the subject.

Yet another aspect of the present invention relates to a method of treating a subject having infantile myofibromatosis. This method involves selecting a subject having a mutation in PDGFRB encoding an amino acid substitution at one or more amino acid residues corresponding to amino acid position 561 and/or 660 of SEQ ID NO:2. The method further involves administering to the selected subject an agent that reduces phosphorylation of PDGFRB under conditions effective to prevent or treat symptoms associated with infantile myofibromatosis in the subject.

In one embodiment of carrying out these methods of the present invention, isolated biological samples from a subject are analyzed for a decrease in RNA and/or protein levels of PDGFRB and/or NOTCH3 compared to protein levels known to exist in normal (non-diseased) individuals. As would be appreciated by a person of ordinary skill in the art, certain gene mutations are known to affect the stability of the mRNA. Nonsense mediated decay is a well recognized mechanism whereby mRNA harboring mutations can be degraded by the cellular machinery. Therefore, gene mutations (most notably stop mutations) result in an absence of mRNA. This will also result in decreased/absent protein. Similarly, some mutant proteins are translated but they may not be stable. For example, their half-life could be markedly decreased resulting in degradation by the proteasome.

In one embodiment, soluble forms of PDGFRB and/or NOTCH3 encoded protein may be detected in various tissues of a subject. Assays used to detect levels of the protein in a sample derived from a subject are well known to those of ordinary skill in the art and include, without limitation, radioimmunoassays, competitive-binding assays, Western blot analysis, and ELISA assay.

An ELISA assay initially comprises preparing an antibody specific to antigens of PDGFRB and/or NOTCH3 encoded protein, preferably a monoclonal antibody. In addition, a reporter antibody is prepared against the monoclonal antibody. To the reporter antibody is attached a detectable reagent such as radioactivity or fluorescence. A sample is then removed from a host and incubated on a solid support, e.g., a polystyrene dish that binds the proteins in the sample. Any free protein binding sites on the dish are then covered by incubating with a non-specific protein such as bovine serum albumin. Next, the monoclonal antibody is incubated in the dish during which time the monoclonal antibodies attach to any PDGFRB and/or NOTCH3 encoded proteins attached to the polystyrene dish. All unbound monoclonal antibody is washed out with buffer. The reporter antibody linked to the detectable reagent is then placed in the dish resulting in binding of the reporter antibody to any monoclonal antibody bound to PDGFRB and/or NOTCH3 encoded proteins. Unattached reporter antibody is then washed out. Substrates are then added to the dish and the amount of signal developed in a given time period is a measurement of the amount of PDGFRB and/or NOTCH3 encoded protein present in a given volume of patient sample when compared against a standard curve.

EXAMPLES

The following examples are provided to illustrate embodiments of the present invention but are by no means intended to limit its scope.

Subjects and Methods for Example 1

Subjects

After informed consent and Institutional Review Board approval from the Icahn School of Medicine of Mount Sinai and the corresponding institutions were obtained, blood samples were obtained from 32 affected individuals, from nine unrelated families with the diagnosis of IM and, where possible, unaffected family members. Clinical diagnoses were provided by the referring physicians. Genomic DNA was extracted with the Puregene kit according to the manufacturer's protocol (Minneapolis, Minn.). Cell lines were established from tumor tissue that was removed from affected individuals as part of their medical care and which was considered pathologic waste.

Whole-Exome Capturing and Sequencing

One unaffected and 11 affected family members, representing nine unrelated kindred, were selected for whole-exome sequencing at the Center for Applied Genomics at The Children's Hospital of Philadelphia. Genomic DNA was isolated from a blood sample by standard methods and randomly sheared to 200-300 bp in size, followed by end-repair, A-tailing, and paired-end index adapter ligation. Whole-exomes were captured using the Agilent SureSelect Human All Exon V4+UTR kit (Agilent Technologies, Santa Clara, Calif., USA) following the manufacturer's protocol. The libraries were subsequently clustered on the cBOT instrument, multiplexing 4 samples per flow cell lane, and sequenced for 101 cycles using a paired-end mode on the Illumina HiSeq2000 following the manufacturer's instructions (Illumina, San Diego, Calif., USA). Base calling and index demultiplexing was performed with the Illumina CASAVA software (version 1.8.2).

Variant Analysis

Sequencing reads were aligned to the human reference genome (UCSC hg19) with Burrows-Wheeler Aligner (BWA, version 0.6.2) (Li et al., "Fast and Accurate Short Read Alignment with Burrows-wheeler Transform," *Bioinformatics* 25:1754-1760 (2009), which is hereby incorporated by reference in its entirety). Optical and PCR duplicates were marked and removed with Picard (version 1.73). Local realignment of reads containing indel sites and base quality score recalibration (BQSR) were performed with the Genome Analysis Tool Kit (GATK, version 2.3) (DePristo et al., "A Framework for Variation Discovery and Genotyping Using Next-generation DNA Sequencing Data," *Nature Genetics* 43:491-498 (2011), which is hereby incorporated by reference in its entirety). Single nucleotide variation ("SNV") and small indels were called with GATK UnifiedGenotyper. Variants were marked as potential sequencing artifacts if the filters on the following annotations were evaluated to be true: (i) for SNVs, "DP<10", "QD<2.0", "MQ<40.0", "FS>60.0", "HaplotypeScore>13.0", "MQRankSum<−12.5", "ReadPosRankSum<−8.0" and (ii) for small indels, "DP<10", "QD<2.0", "ReadPosRankSum<−20.0", "InbreedingCoeff<−0.8", "FS>200.0". The kinship coefficient was calculated for each sample using KING (Manichaikul et al., "Robust Relationship Inference in Genome-wide Association Studies," *Bioinformatics* 26:2867-2873 (2010), which is hereby incorporated by reference in its entirety) to confirm reported relationships and identify cryptic relationships among samples. ANNOVAR (Wang et al., "ANNOVAR: Functional Annotation of Genetic Variants from Next-generation Sequencing Data," *Nucleic Acids Research* 38:e164 (2010), which is hereby incorporated by reference in its entirety) and SnpEff (version 2.0.5) (Cingolani et al., "A Program for Annotating and Predicting the Effects of Single Nucleotide Polymorphisms, SnpEff: SNPs in the Genome of *Drosophila melanogaster* Strain w1118; iso-2; iso-3,*" Fly* 6:2 (2012), which is hereby incorporated by reference in its entirety) were used for annotating variants. Human Gene Mutation Database (HGMD) (Stenson et al., "The Human Gene Mutation Database (HGMD): 2008 Update," *Genome Med.* 1:13 (2009), which is hereby incorporated by reference in its entirety) was used for annotating known genes and mutations for human inherited diseases. Prediction scores from SIFT (Kumar et al., "Predicting the Effects of Coding Non-synonymous Variants on Protein Function Using the SIFT Algorithm," *Nat. Protoc.* 4:1073-1081 (2009), which is hereby incorporated by reference in its entirety), Polyphen2 (Adzhubei et al., "A Method and Server for Predicting Damaging Missense Mutations," *Nat. Methods* 7:248-249 (2010), which is hereby incorporated by reference in its entirety), LRT (Chun et al., "Identification of Deleterious Mutations Within Three Human Genomes," *Genome Res.* 19:1553-1561 (2009), which is hereby incorporated by reference in its entirety), and MutationTaster (Schwarz et al., "Mutation Taster Evaluates Disease-causing Potential of Sequence Alterations," *Nat. Methods* 7:575-576 (2010), which is hereby incorporated by reference in its entirety), along with conservation scores PhyloP (Siepel et al., "New Methods for Detecting Lineage-specific Selection," *Proceedings of the 10th International Conference on Research in Computational Molecular Biology (RECOMB* 2006) pp. 190-205 (2006), which is hereby incorporated by reference in its entirety) and GERP++ (Davydov et al., "Identifying a High Fraction of the Human Genome to be Under Selective Constraint Using GERP++," *PLoS Comput. Biol.* 6:e1001025 (2010), which is hereby incorporated by reference in its entirety) for every potential nonsynonymous SNV in the human genome were retrieved from dbNSFP (database for nonsynonymous SNPs' functional predictions) (Liu et al., "dbNSFP: A Lightweight Database of Human Non-synonymous SNPs and Their Functional Predictions," *Hum. Mutat.* 32:894-899 (2011), which is hereby incorporated by reference in its entirety). SNVs and indels were selected as potential pathogenic variants if they met all the following criteria: (i) heterozygous; (ii) not previously described or rare (minor allele frequency (MAF)<0.5%) in a control cohort of more than 9000 control individuals (1000 genomes project, April 2012 release; 6503 exomes from NHLBI GO Exome Sequencing Project (ESP6500SI), and 1200 in-house whole-exomes; (iii) nonsynonymous, or splice acceptor and donor site SNVs, or frameshift coding indels (NS/SS/I); (iv) predicted to be deleterious by at least 3 prediction methods, i.e., SIFT, PolyPhen2, MutationTaster, and LRT; and (v) conserved PhyloP score and GERP++ score >2.0. Variants were also analyzed using the Ingenuity Variant Analysis web-based application.

Sanger Sequencing Validation

Sanger sequencing of the variants was performed with ABI BigDye Terminator Cycle Sequencing Kit on an ABI 3730 sequencer. It was performed using the standard techniques of PCR amlicons with the following primers:

```
(i) c.4556T > C (p.Leu1519Pro) in NOTCH3
(RefSeq NM_000435):
                                    (SEQ ID NO: 5)
5'-GTCACTCACCCGATCACCTC-3'
and
                                    (SEQ ID NO: 6)
5'-AGCCCGGTGTACGAGAAGTA-3';
```

-continued (ii) c.1978C > A (p.Pro660Thr) in PDGFRB
(RefSeq NM_002609):

(SEQ ID NO: 7)
5'-CTCCCACGTGGAGTCATAGG-3'
and (SEQ ID NO: 8)
5'-TGTCCTAGACGGACGAACCT-3';

(iii) c.1681C > T (p.Arg561Cys) in PDGFRB
(RefSeq NM_002609):

(SEQ ID NO: 9)
5'-CAGCAGGAGTGTGCTGTTGT-3'
and (SEQ ID NO: 10)
5'-CGGGGCAGAAGAGTCAGAAT-3'.

Cell Culture

Cells were maintained in complete media: DMEM-F12 (Invitrogen) with 10% FBS (Atlanta Biologicals) with ABAM and Gentamicin (Sigma). For immunocytochemistry cells were plated on 10 µg/ml collagen in supplemented serum-free media (SSFM): DMEM-F12 plus RPMI-1640 Vitamin Mix, ITS Liquid media supplement, 1 mg/ml glutathione; 2 mM L-glutamine, 1 mM sodium pyruvate, 0.1 mM MEM non-essential amino acids; with ABAM and Gentamicin (Ng et al., "Exome Sequencing Identifies the Cause of a Mendelian Disorder," Nat. Genet. 42:30-35 (2010), which is hereby incorporated by reference in its entirety).

Immunocytochemistry

Cells were fixed with 3% p-formaldehyde (Fisher Scientific, Fair Lawn, N.J.) and permeabilized with 0.1% Triton X-100 (Sigma). After blocking with 3% normal mouse serum (Jackson Immuno Research), cells were incubated with vimentin antibody (rabbit) and a-SMA antibody (mouse) (Sigma) followed by secondary antibodies-Alexa 488 (vimentin) or Alexa-568 (a-SMA). Coverslips were viewed with a Zeiss Axioskop microscope and images were captured using a Zeiss Axioscope with a SPOT-2 CCD camera (Diagnostic Instruments, Sterling Heights, Mich.) and processed by Adobe PhotoShop software).

Example 1—Exome Sequencing Identifies Mutations in PDGFRB and NOTCH3 as Causes of Autosomal Dominant Infantile Myofibromatosis Results Exome capturing and sequencing was originally performed on nine probands from the nine unrelated IM families (FIG. 1). Agilent SureSelect was used to prepare libraries for paired-end sequencing (2×101 bp) on Illumina HiSeq 2000 sequencers. On average, 9.7 Gb of sequences were produced for each sample. 97% of the reads were mappable to the human reference genome (hg19), and 94% of targeted exome had at least 10× depth of coverage. The mean depth of coverage was 74-fold.

Figure 2:
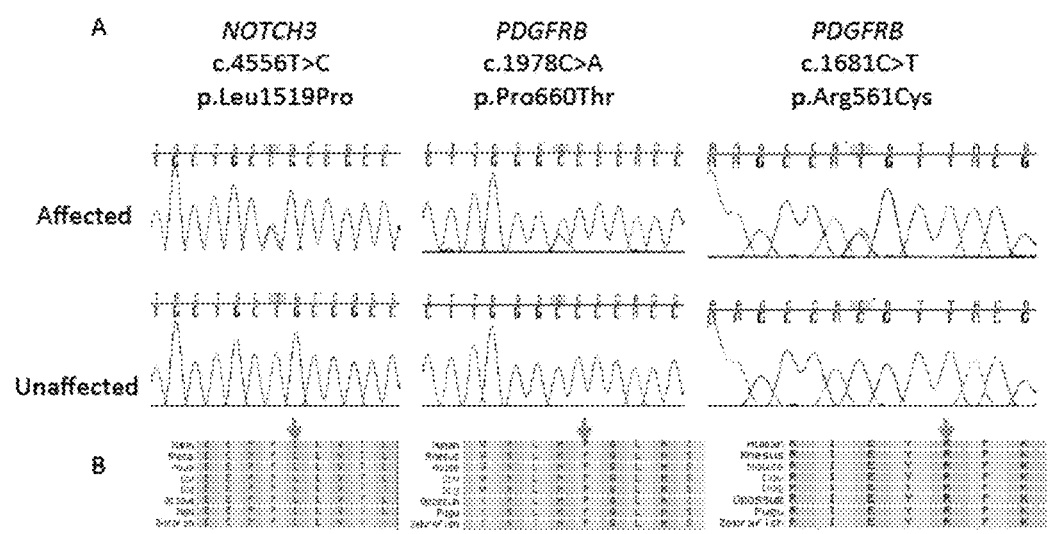
FIGS. 2A-B relate to the identification of mutations in PDGFRB and NOTCH3.
Figure 4:
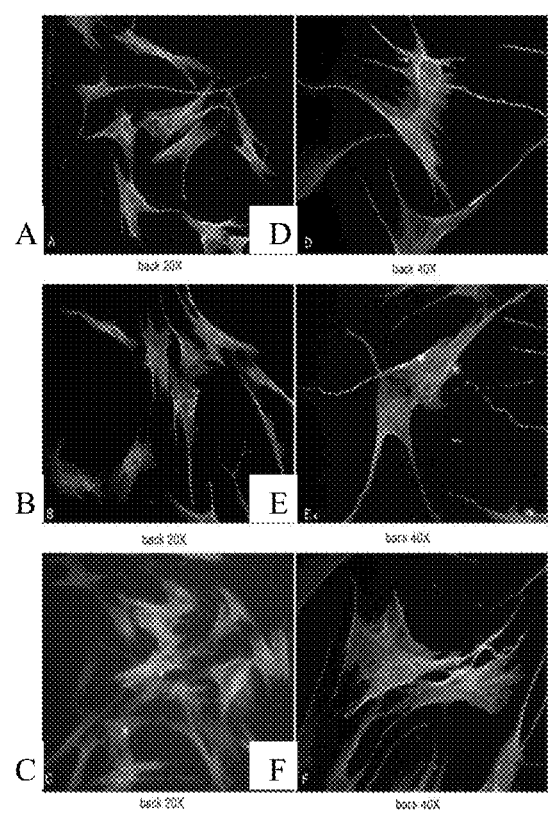
FIGS. 4A-F are photographs illustrating patient-derived tumor cell lines that demonstrate a myofibroblastic phenotype. Illustrated are vimentin and α-SMA staining of patient-derived tumor cell lines from family 9. Cells were cultured from a soft-tissue tumor excised from an affected area on the patient's back as part of their care. Three paired 20× (FIGS. 4A-C) and 40× (FIGS. 4D-F) views are shown.
Figures 5, 6:
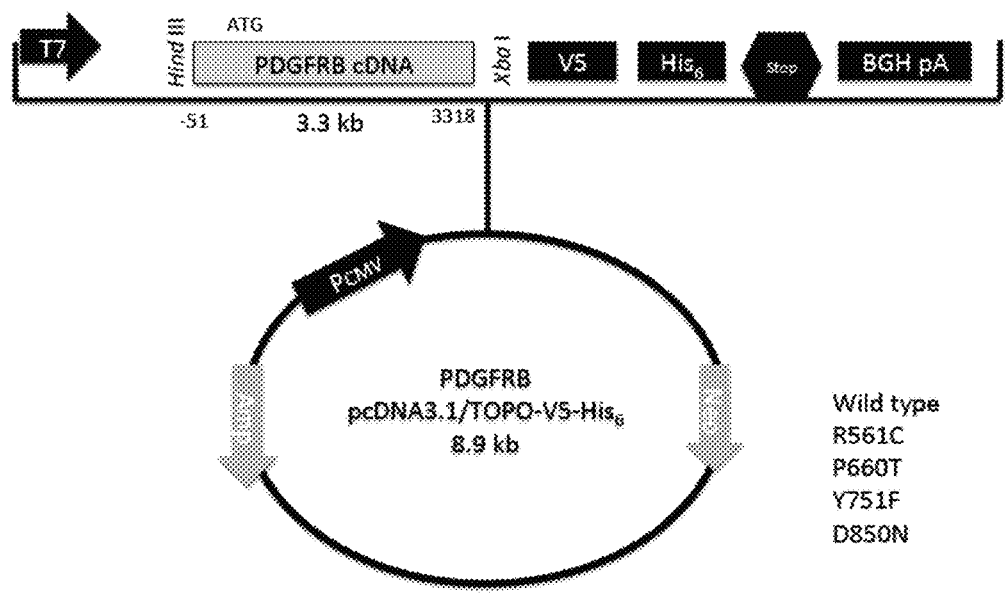
FIG. 5 is a table showing rare variants in PDGFRB and NOTCH3 identified in 9 IM families for WES.
FIG. 6 is a schematic illustration of the transient expression plasmid pcDNA3.1/TOPO-V5-His$_6$ for expression PDGFRB clones.

A total of 195,651 SNVs and 20,700 indels were identified, of which 178,991 SNVs (91%) and 17,238 indels (83%) were reported in dbSNP135. On average, 82,855 SNVs and 11,882 indels were called per sample. The filtering strategy was applied to focus on a subset of potentially pathogenic variants (Ng et al., "Exome Sequencing Identifies the Cause of a Mendelian Disorder," Nat. Genet. 42:30-35 (2010), which is hereby incorporated by reference in its entirety). Variants were filtered by mode of inheritance, variant quality, conservation, predicted deleterious scores, and allele frequency in the public and in-house whole exomes. Two missense variants in PDGFRB (MIM 173410; NM_002609.3, which are hereby incorporated by reference in their entirety) were present in eight members in eight families. No PDGFRB mutations were identified in family 9 (FIG. 5). Sanger sequencing of all available family members, affected and unaffected, in the eight families revealed that the two PDGFRB variants segregated appropriately with disease status (FIG. 2). In family IM-9, in which no PDGFRB mutations were identified, two other affected and one unaffected individual from this kindred were exome sequenced. Variants in NOTCH3 (MIM 600276; NM_000435.2, which are hereby incorporated by reference in their entirety) and PET112 (MIM 603645; NM_004564.2, which are hereby incorporated by reference in their entirety) were found in all three affected members but not in the unaffected family member (FIG. 5). Sanger sequencing of 16 family members, consisting of nine affected and seven unaffected individuals, revealed that only the NOTCH3 mutation c.4556T>C (p.Leu1519Pro) segregated appropriately with affected status (FIG. 2). Given the unexpected finding of candidate disease-causing mutations in a second gene, the histologic findings were re-examined in a soft tissue tumor isolated from this family and also a cell line was generated from affected tissue (Wang et al., "Degradation of Internalized avb5 Integrin is Controlled by uPAR Bound uPA: Effect on b1 Integrin Activity and α-SMA Stress Fiber Assembly," PLoS One 7:e33915 (2012), which is hereby incorporated by reference in its entirety). Histopathologic analysis was consistent with the diagnosis of IM and staining with α-SMA further demonstrated the tumor's myofibroblastic nature (FIG. 4).

All three rare missense variants in both genes were predicted to be damaging with high probability using the prediction algorithms LRT, MutationTaster, Polyphen2, and SIFT and they were located in highly conserved exonic regions. In PDGFRB, c.1978C>A (p.Pro660Thr) is a heterozygous missense variant in exon 14. It is located in the tyrosine kinase domain of the protein. The variant was present in the ESP6500SI dataset with a MAF of 0.000077. It was reported in dbSNP135 (r5144050370), but was not found in the 1000 genomes project, the catalogue of somatic mutations in cancer (COSMIC v63), nor in a database of approximately 1200 in-house sequenced whole-exomes. The second PDGFRB variant, c.1681C>T(p.Arg561Cys), is a heterozygous missense variant in exon 12. It is not present in the publically available databases nor in the approximately 9000 public and in-house whole-exome datasets. For family IM-9, the NOTCH3 variant C.4556T>C (p.Leu1519Pro) predicts a heterozygous missense variant in exon 25. It is a newly described variant, not present in public databases and in-house whole-exomes. It is located in the protein's highly conserved hetero-dimerization domain.

Discussion

By exome sequencing, three missense mutations have been identified in two genes causing autosomal dominant IM in nine unrelated families, i.e., c.1978C>A (p.Pro660Thr) and c.1681C>T (p.Arg561Cys) in PDGFRB, and c.4556T>C (p.Leu1519Pro) in NOTCH3 (FIG. 3).

In the current study, two missense mutations in PDGFRB were identified in eight IM families. PDGFRB, located on 5q32, encodes the platelet-derived growth factor receptor-beta. It is a cell surface tyrosine kinase receptor for members of the platelet-derived growth factor family (PDGF A, B, C, and D), which are mitogens for cells of mesenchymal origin. Activation of the receptor leads to its dimerization, autophosphorylation of tyrosine residues, and to activation of downstream signaling pathways, inducing cellular proliferation, differentiation, survival, and migration. PDGFRB is expressed in neurons, plexus choroideus, vascular smooth muscle cells (VSMCs), and pericytes. PDGFRB signal transduction is required for proliferation and migration of a subset of VSMCs. PDGFRB signaling has been well established in early hematopoiesis and blood vessel formation (Demoulin et al., "Platelet-derived Growth Factors and Their Receptors in Normal and Malignant Hematopoiesis," Am. J. Blood. Res. 2:44-56 (2012), which is hereby incorporated by reference in its entirety). Enhanced PDGF-PDGFR signaling is a hallmark in a variety of diseases, including cancers, atherosclerosis, pulmonary fibrosis, and restenosis. Recently, a missense mutation, c.1973T>C (p.Leu658Pro) in PDGFRB, was reported to be a recently identified cause of idiopathic basal ganglia calcification (IBGC) (Nicolas et al., "Mutation of the PDGFRB Gene as a Cause of Idiopathic Basal Ganglia Calcification," Neurology 80:1-7 (2013), which is hereby incorporated by reference in its entirety).

One novel missense mutation c.4556T>C (Leu1519Pro) in NOTCH3 was identified as the most probable causative mutation for one IM family. NOTCH3 encodes the third discovered human homologue of the Drosophila melanogaster type I membrane protein notch. Notch signaling allows cells to coordinate fate decisions in metazoan development. Notch signals are highly pleiotropic, dictating cellular fates in a way that depends on cellular context. NOTCH3 is primarily expressed in adult arterial vascular smooth muscle cells (VSMCs) in large conduit, pulmonary, and systemic resistance arteries. Mutations in NOTCH3 have also been identified as the underlying cause of cerebral autosomal dominant arteriopathy with subcortical infarcts and leukoencephalopathy (CADASIL) (Joutel et al., "Notch3 Mutations in CADASIL, a Hereditary Adult-onset Condition Causing Stroke and Dementia," Nature 383:707-710 (1996), which is hereby incorporated by reference in its entirety). The NOTCH3 IM family members are notable for possessing multiple, recurrent soft tissue lesions and have no reported clinical history consistent with a diagnosis of CADASIL. The majority of reported CADASIL-associated mutations are located in the epidermal growth factor-like (EGF-like) domain in the extra-cellular domain of the protein (exons 2-24). A novel heterozygous missense mutation (c.4544T>C, p.Leu1515Pro) was recently reported in exon 25, a highly conserved hetero-dimerization domain of Notch3, in a patient with cerebral small-vessel-disease but lacking typical deposits and Notch3 accumulation (Fouillade et al., "Activating NOTCH3 Mutation in a Patient with Small-vessel-disease of the Brain," Hum. Mutat. 29:452 (2008), which is hereby incorporated by reference in its entirety). Biochemical analysis suggests that the c.4544T>C (p.Leu1515Pro) mutation renders Notch3 hyperactive through destabilization of the heterodimer. The novel mutation c.4556T>C (p.Leu1519Pro) identified in an IM family was located close to the Leu1515Pro substitution.

Of particular interest in trying to understand how mutations in two different genes, PDGFRB and NOTCH3, could result in the same disease, a possible mechanistic link was recently provided (Jin et al., "Notch Signaling Regulates Platelet-derived Growth Factor Receptor-beta Expression in Vascular Smooth Muscle Cells," Circ. Res. 102:1483-1491 (2008), which is hereby incorporated by reference in its entirety). Specifically, it was demonstrated that PDGFRB was a previously unrecognized and immediate Notch3 target gene (Jin et al., "Notch Signaling Regulates Platelet-derived Growth Factor Receptor-beta Expression in Vascular Smooth Muscle Cells," Circ. Res. 102:1483-1491 (2008), which is hereby incorporated by reference in its entirety). PDGFRB expression was upregulated by Notch3 ligand induction or by activated forms of the Notch3 receptor. The availability of established tumor cell lines from patients will allow direct exploration of this mechanistic link. In view of the IM disease-causing mutations in PDGFRB and NOTCH3 demonstrated herein, modulation of PDGFRB and/or NOTCH3 provide a targeted therapeutic strategy.

In conclusion, these studies indicate that PDGFRB mutations are a case of autosomal dominant IM, a genetically heterogeneous disease with incomplete penetrance and variable expressivity. These studies have also identified a single family with a germline NOTCH3 mutation.

Example 2—Transient Expression of Mutant PDGFRB

PDGFRB cDNAs were cloned into transient expression plasmid pcDNA3.1/TOPO-V5-His$_6$ (FIG. 6) to produce wildtype clones, IMF-causing clones (i.e., R561C and P660T mutants), and loss-of-function PDGFRB mutant Y751F and gain-of-function PDGFRB mutant D850N.

Cloning was carried out in COS7 cells using the XtremeGene transfection reagent, 1 µg of DNA and 3 µg of reagent per one 6-well plate well. Cells were incubated for 24-48 hours. Cells were starved with serum-free medium for 17 hours. Cells were stimulated with PDGF-BB (50 ng/ml) for 30 minutes. Cell pellets were collected. Cells were then lysed.

Figure 7:
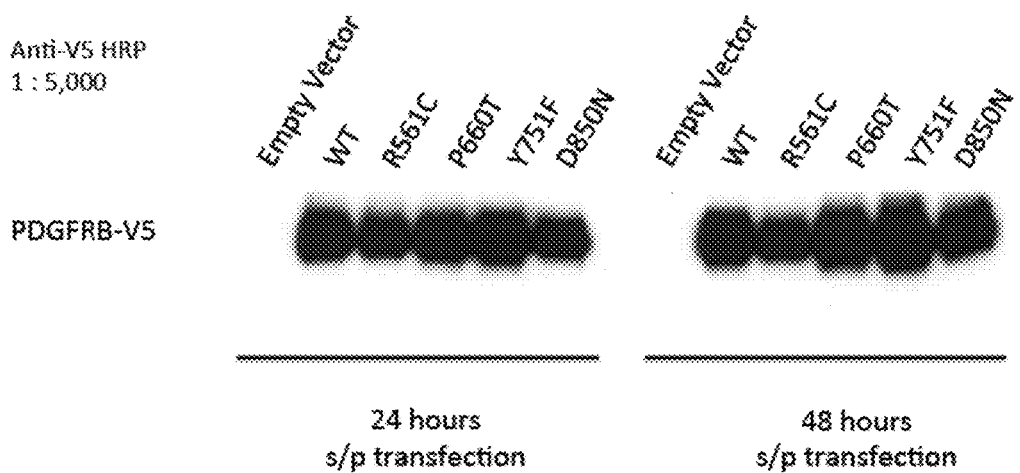
FIG. 7 is a photograph of results of an expression study carried out to detect V5 tagged protein.

An expression study was carried out to detect V5 tagged protein, the results of which are illustrated in FIG. 7.

Figure 8A:
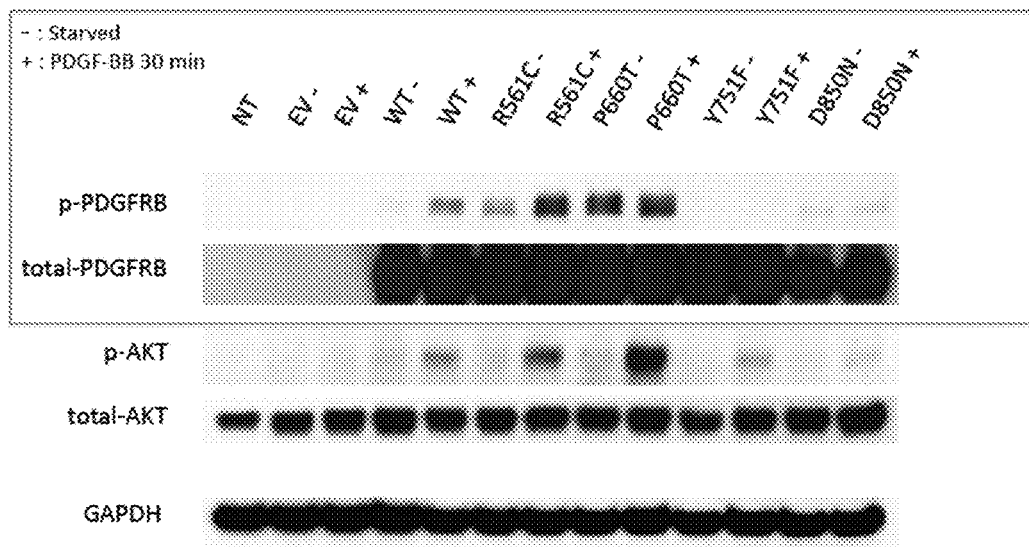
FIGS. 8A and 8B illustrate results using anti-p-PDGFRB and anti-pAKT antibodies. In a transient expression system, the two PDGFRB mutations are activating mutations, which result in autophosphorylation of PDGFRB, in the absence of PDGF-BB.
Figure 8B:
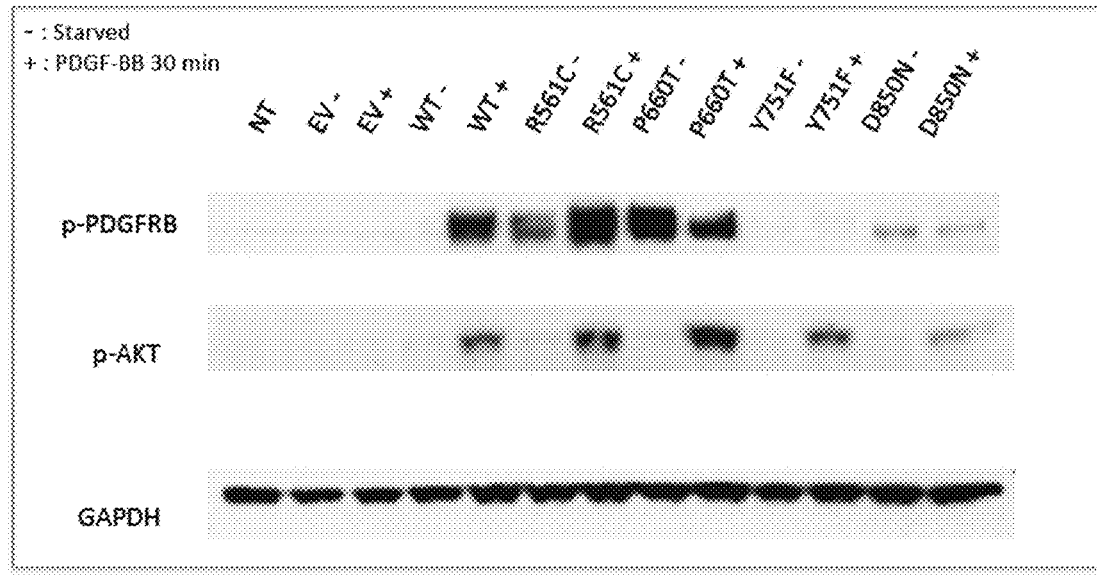

Results using anti-PDGFRB, anti-p-PDGFRB, and anti-pAKT antibodies are set forth in FIGS. 8A-B. In a transient expression system, the two PDGFRB mutations described herein are activating mutations, which result in autophosphorylation of PDGFRB, in the absence of PDGF-BB.

Example 3—Treatment with Imatinib Blocks Activation of IMF Gain-of-Function Mutants Transient expression of PDGFRB mutants was carried out using plasmid pcDNA3.1/TOPO-V5-His$_6$, as described supra.

Figure 9:
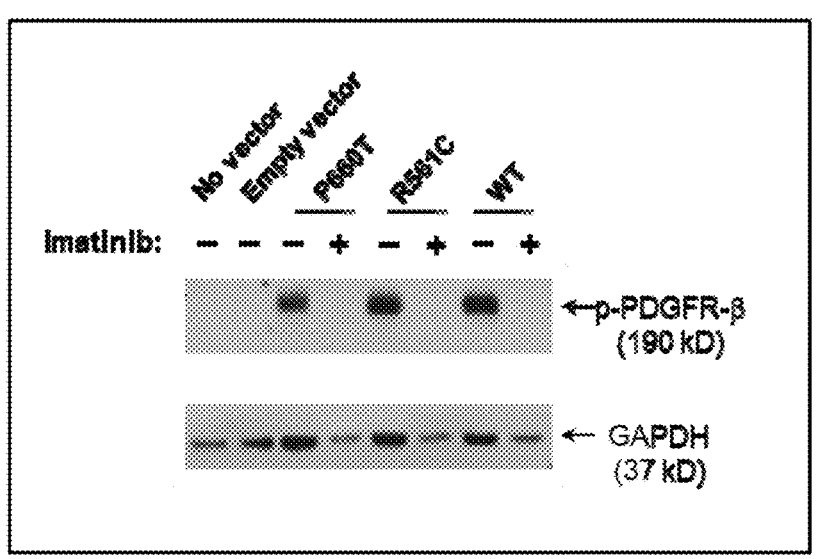
FIG. 9 is a photograph showing results of treatment with Imatinib, which demonstrates that Imatinib blocks activation of IMF gain-of-function mutants.

Treatment with Imatinib was shown to block activation of IMF gain-of-function mutants. Specifically, Imatinib (Selleckchem) was prepared to a 10 mM stock by dissolving dH$_2$O and filtering through a 0.22 µm filter. PDGFRB from Cell Signaling was used at 1:1000 overnight incubation. Lysates were collected 7.5 hours after treatment with 10 µm Imatinib. 50 of lysate was loaded on gels for electrophoresis/Western blotting. Results are shown in FIG. 9. The antibodies used in the Western to image p-PDGFRB and PDGFRB were Phospho-PDGF Receptor beta (Tyr751) (C63G6) Rabbit mAB #4549 and PDGF Receptor beta (28E1) Rabbit mAb #3169, respectively. These results indicate that Gleevec was able to reduce the phosphorylation of PDGFRB for both the mutants and wt PDGFRB.

All of the features described herein (including any accompanying claims, abstract and drawings), and/or all of the steps of any method or process so disclosed, may be combined with any of the above aspects in any combination, except combinations where at least some of such features and/or steps are mutually exclusive.

What is claimed:

1. A method of detecting one or more missense mutations in PDGFRB and/or NOTCH3, said method comprising:
   (I) (a) providing an isolated nucleic acid sample from the subject;
   (b) contacting the sample with one or more reagents suitable for detecting the presence of one or more missense mutations in PDGFRB and/or NOTCH3, wherein the one or more mutation in PDGFRB encodes an amino acid substitution at one or more amino acid residues corresponding to amino acid position 561 and/or 660 of SEQ ID NO:2, and wherein the one or more mutation in NOTCH3 encodes an amino acid substitution at an amino acid residue corresponding to amino acid position 1519 of SEQ ID NO:4;
   (c) detecting, in the sample, the presence of the one or more mutations in PDGFRB and/or NOTCH3 based on said contacting; and/or
   (II) (a) providing an isolated protein sample from the subject,
   (b) contacting the sample with one or more antibodies suitable for detecting the presence of one or more missense mutations in PDGFRB and/or NOTCH3, wherein the one or more mutation in PDGFRB encodes an amino acid substitution at one or more amino acid residues corresponding to amino acid position 561 and/or 660 of SEQ ID NO:2, and wherein the one or more mutation in NOTCH3 encodes an amino acid substitution at an amino acid residue corresponding to amino acid position 1519 of SEQ ID NO:4; and
   (c) detecting, in the sample, the presence of the one or more mutations in PDGFRB and/or NOTCH3 based on the antibody binding to the protein in the sample.

2. A method of treating a subject having one or more missense mutations in PDGFRB and/or NOTCH3, said method comprising:
   (I) (a) providing an isolated nucleic acid sample from the subject;
   (b) contacting the sample with one or more reagents suitable for detecting the presence of one or more missense mutations in PDGFRB and/or NOTCH3, wherein the one or more mutation in PDGFRB encodes an amino acid substitution at one or more amino acid residues corresponding to amino acid position 561 and/or 660 of SEQ ID NO:2, and wherein the one or more mutation in NOTCH3 encodes an amino acid substitution at an amino acid residue corresponding to amino acid position 1519 of SEQ ID NO:4; and (c) detecting, in the sample, the presence of the one or more mutations in PDGFRB and/or NOTCH3 based on said contacting; and/or (II) (a) providing an isolated protein sample from the subject, (b) contacting the sample with one or more antibodies suitable for detecting the presence of one or more missense mutations in PDGFRB and/or NOTCH3, wherein the one or more mutation in PDGFRB encodes an amino acid substitution at one or more amino acid residues corresponding to amino acid position 561 and/or 660 of SEQ ID NO:2, and wherein the one or more mutation in NOTCH3 encodes an amino acid substitution at an amino acid residue corresponding to amino acid position 1519 of SEQ ID NO:4;

(c) detecting, in the sample, the presence of the one or more mutations in PDGFRB and/or NOTCH based on the antibody binding to the protein in the sample; and administering a therapy suitable for treatment of infantile myofibromatosis to a subject identified as having one or more missense mutations in PDGFRB and/or NOTCH3.

3. The method according to claim 2, wherein the biological sample comprises a blood sample.

4. The method according to claim 2, wherein the therapy is selected from the group consisting of removal of a tumor, administering radiation therapy, and modulating PDGFRB and/or NOTCH3 gene expression and/or PDGFRB and/or NOTCH3 encoded protein activity.

5. The method according to claim 2, wherein the therapy comprises administering an agent selected from Imatinib, Covitinib (TKI-258), Linifanib (ABT-869), and Motesanib Diphosphate (AMG-706).

6. The method according to claim 2, wherein the therapy is Imatinib.

7. The method according to claim 2, wherein the method comprises preventing or treating symptoms associated with infantile myofibromatosis.

8. A method of detecting the presence or absence of one or more missense mutations in PDGFRB and/or NOTCH3 in a subject comprising:

a) providing an isolated biological sample from the subject;

b) contacting the sample with i) an antibody that specifically detects PDGFRB having a missense mutation, wherein the missense mutation is a substitution at an amino acid residue corresponding to amino acid position 561 and/or 660 of SEQ ID NO:2; and/or ii) an antibody that specifically detects NOTCH3 having a missense mutation, wherein the missense mutation is a substitution at an amino acid residue corresponding to amino acid position 1519 of SEQ ID NO:4; and c) detecting binding or absence of binding of the antibody to the sample, wherein binding is indicative of the presence of PDGFRB and/or NOTCH3 having said missense mutations, and lack of binding is indicative of the absence of PDGFRB and/or NOTCH3 having said missense mutations.

9. The method according to claim 8, wherein the method comprises radioimmunoassay, competitive-binding assay, Western blot analysis, and/or ELISA assay.

10. The method according to claim 8, wherein the antibody is a monoclonal antibody.

11. The method according to claim 8, wherein detecting binding or absence of binding of the antibody to the sample comprises using a detectable reagent.

12. The method according to claim 11, wherein the detectable reagent is radioactivity or fluorescence.

13. The method according to claim 8 further comprising the step of comparing the level of binding of PDGFRB and/or NOTCH3 in the sample against a standard curve or normal levels of PDGFRB and/or NOTCH3.

* * * * *

SEQUENCE LISTING

<160> NUMBER OF SEQ ID NOS: 10

<210> SEQ ID NO 1
<211> LENGTH: 5718
<212> TYPE: DNA
<213> ORGANISM: Homo sapiens

<400> SEQUENCE: 1

| | | | | | |
|---|---|---|---|---|---|
| ctcctgaggc | tgccagcagc | cagcagtgac | tgcccgccct | atctgggacc | caggatcgct | 60 |
| ctgtgagcaa | cttggagcca | gagaggagat | caacaaggag | gaggagagag | ccggcccctc | 120 |
| agccctgctg | cccagcagca | gcctgtgctc | gccctgccca | acgcagacag | ccagacccag | 180 |
| ggcggcccct | ctggcggctc | tgctcctccc | gaaggatgct | ggggagtga | ggcgaagctg | 240 |
| ggccgctcct | ctcccctaca | gcagcccct | tcctccatcc | ctctgttctc | ctgagccttc | 300 |
| aggagcctgc | accagtcctg | cctgtccttc | tactcagctg | ttacccactc | tgggaccagc | 360 |
| agtcttttctg | ataactggga | gagggcagta | aggaggactt | cctggagggg | gtgactgtcc | 420 |
| agagcctgga | actgtgccca | caccagaagc | catcagcagc | aaggacacca | tgcggcttcc | 480 |
| gggtgcgatg | ccagctctgg | ccctcaaagg | cgagctgctg | ttgctgtctc | tcctgttact | 540 |
| tctggaacca | cagatctctc | agggcctggt | cgtcacaccc | ccggggccag | agcttgtcct | 600 |
| caatgtctcc | agcaccttcg | ttctgacctg | ctcgggttca | gctccggtgg | tgtgggaacg | 660 |
| gatgtcccag | gagcccccac | aggaaatggc | caaggcccag | gatggcacct | tctccagcgt | 720 |
| gctcacactg | accaacctca | ctgggctaga | cacgggagaa | tacttttgca | cccacaatga | 780 |
| ctcccgtgga | ctggagaccg | atgagcggaa | acggctctac | atctttgtgc | cagatccac | 840 |
| cgtgggcttc | ctccctaatg | atgccgagga | actattcatc | tttctcacgg | aaataactga | 900 |
| gatcaccatt | ccatgccgag | taacagaccc | acagctggtg | gtgacactgc | acgagaagaa | 960 |
| aggggacgtt | gcactgcctg | tcccctatga | tcaccaacgt | ggcttttctg | gtatctttga | 1020 |
| ggacagaagc | tacatctgca | aaaccaccat | tggggacagg | gaggtggatt | ctgatgccta | 1080 |
| ctatgtctac | agactccagg | tgtcatccat | caacgtctct | gtgaacgcag | tgcagactgt | 1140 |
| ggtccgccag | ggtgagaaca | tcaccctcat | gtgcattgtg | atcgggaatg | aggtggtcaa | 1200 |
| cttcgagtgg | acatacccccc | gcaaagaaag | tgggcggctg | gtggagccgg | tgactgactt | 1260 |
| cctcttggat | atgccttacc | acatccgctc | catcctgcac | atccccagtg | ccgagttaga | 1320 |
| agactcgggg | acctacacct | gcaatgtgac | ggagagtgtg | aatgaccatc | aggatgaaaa | 1380 |
| ggccatcaac | atcaccgtgg | ttgagagcgg | ctacgtgcgg | ctcctgggag | aggtgggcac | 1440 |
| actacaattt | gctgagctgc | atcggagccg | gacactgcag | gtagtgttcg | aggcctaccc | 1500 |
| accgcccact | gtcctgtggt | tcaaagacaa | ccgcacccctg | ggcgactcca | gcgctggcga | 1560 |
| aatcgccctg | tccacgcgca | acgtgtcgga | gacccggtat | gtgtcagagc | tgacactggt | 1620 |
| tcgcgtgaag | gtggcagagg | ctggccacta | caccatgcgg | gccttccatg | aggatgctga | 1680 |
| ggtccagctc | tccttccagc | tacagatcaa | tgtccctgtc | cgagtgctgg | agctaagtga | 1740 |
| gagccacct | gacagtgggg | aacagacagt | ccgctgtcgt | ggccggggca | tgccccagcc | 1800 |
| gaacatcatc | tggtctgcct | gcagagacct | caaaaggtgt | ccacgtgagc | tgccgcccac | 1860 |
| gctgctgggg | aacagttccg | aagaggagag | ccagctggag | actaacgtga | cgtactggga | 1920 |
| ggaggagcag | gagtttgagg | tggtgagcac | actgcgtctg | cagcacgtgg | atcggccact | 1980 |
| gtcggtgcgc | tgcacgctgc | gcaacgctgt | gggccaggac | acgcaggagg | tcatcgtggt | 2040 |
| gccacactcc | ttgcccttta | aggtggtggt | gatctcagcc | atcctggccc | tggtggtgct | 2100 |

-continued

```
caccatcatc tcccttatca tcctcatcat gctttggcag aagaagccac gttacgagat      2160
ccgatggaag gtgattgagt ctgtgagctc tgacggccat gagtacatct acgtggaccc      2220
catgcagctg ccctatgact ccacgtggga gctgccgcgg gaccagcttg tgctgggacg      2280
caccctcggc tctggggcct ttgggcaggt ggtggaggcc acggctcatg gcctgagcca      2340
ttctcaggcc acgatgaaag tggccgtcaa gatgcttaaa tccacagccc gcagcagtga      2400
gaagcaagcc cttatgtcgg agctgaagat catgagtcac cttgggcccc acctgaacgt      2460
ggtcaacctg ttgggggcct gcaccaaagg aggacccatc tatatcatca ctgagtactg      2520
ccgctacgga gacctggtgg actacctgca ccgcaacaaa cacaccttcc tgcagcacca      2580
ctccgacaag cgccgcccgc ccagcgcgga gctctacagc aatgctctgc ccgttgggct      2640
cccccctgccc agccatgtgt ccttgaccgg ggagagcgac ggtggctaca tggacatgag      2700
caaggacgag tcggtggact atgtgcccat gctggacatg aaaggagacg tcaaatatgc      2760
agacatcgag tcctccaact acatggcccc ttacgataac tacgttccct ctgcccctga      2820
gaggacctgc cgagcaactt tgatcaacga gtctccagtg ctaagctaca tggacctcgt      2880
gggcttcagc taccaggtgg ccaatggcat ggagtttctg cctccaaga actgcgtcca      2940
cagagacctg gcggctagga acgtgctcat ctgtgaaggc aagctggtca agatctgtga      3000
ctttggcctg gctcgagaca tcatgcggga ctcgaattac atctccaaag gcagcacctt      3060
tttgcctttta aagtggatgg ctccggagag catcttcaac agcctctaca ccaccctgag      3120
cgacgtgtgg tccttcggga tcctgctctg ggagatcttc accttgggtg caccccttta      3180
cccagagctg cccatgaacg agcagttcta caatgccatc aaacgggggtt accgcatggc      3240
ccagcctgcc catgcctccg acgagatcta tgagatcatg cagaagtgct gggaagagaa      3300
gtttgagatt cggcccccct tctcccagct ggtgctgctt ctcgagagac tgttgggcga      3360
aggttacaaa aagaagtacc agcaggtgga tgaggagttt ctgaggagtg accacccagc      3420
catccttcgg tcccaggccc gcttgcctgg gttccatggc ctccgatctc ccctggacac      3480
cagctccgtc ctctatactg ccgtgcagcc caatgagggt gacaacgact atatcatccc      3540
cctgcctgac cccaaacccg aggttgctga cgagggccca ctggagggtt ccccagcct      3600
agccagctcc accctgaatg aagtcaacac ctcctcaacc atctcctgtg acagccccct      3660
ggagccccag gacgaaccag agccagagcc ccagcttgag ctccaggtgg agccggagcc      3720
agagctggaa cagttgccgg attcggggtg ccctgcgcct cgggcggaag cagaggatag      3780
cttcctgtag ggggctggcc cctaccctgc cctgcctgaa gctccccccc tgccagcacc      3840
cagcatctcc tggcctggcc tgaccgggct tcctgtcagc caggctgccc ttatcagctg      3900
tccccttctg gaagctttct gctcctgacg tgttgtgccc caaaccctgg ggctggctta      3960
ggaggcaaga aaactgcagg ggccgtgacc agccctctgc ctccagggag gccaactgac      4020
tctgagccag ggttccccca gggaactcag ttttcccata tgtaagatgg gaaagttagg      4080
cttgatgacc cagaatctag gattctctcc ctggctgaca ggtggggaga ccgaatccct      4140
ccctgggaag attcttggag ttactgaggt ggtaaattaa cttttttctg ttcagccagc      4200
tacccctcaa ggaatcatag ctctctcctc gcacttttat ccaccaggaa gctagggaag      4260
agaccctagc ctccctggct gctggctgag ctagggccta gccttgagca gtgttgcctc      4320
atccagaaga aagccagtct cctccctatg atgccagtcc ctgcgttccc tggcccgagc      4380
tggtctgggg ccattaggca gcctaattaa tgctggaggc tgagccaagt acaggacacc      4440
```

| | |
|---|---|
| cccagcctgc agcccttgcc cagggcactt ggagcacacg cagccatagc aagtgcctgt | 4500 |
| gtccctgtcc ttcaggccca tcagtcctgg ggcttttttct ttatcaccct cagtcttaat | 4560 |
| ccatccacca gagtctagaa ggccagacgg gccccgcatc tgtgatgaga atgtaaatgt | 4620 |
| gccagtgtgg agtggccacg tgtgtgtgcc agtatatggc cctggctctg cattggacct | 4680 |
| gctatgaggc tttggaggaa tccctcaccc tctctgggcc tcagtttccc cttcaaaaaa | 4740 |
| tgaataagtc ggacttatta actctgagtg ccttgccagc actaacattc tagagtattc | 4800 |
| caggtggttg cacatttgtc cagatgaagc aaggccatat accctaaact tccatcctgg | 4860 |
| gggtcagctg ggctcctggg agattccaga tcacacatca cactctgggg actcaggaac | 4920 |
| catgcccctt ccccaggccc ccagcaagtc tcaagaacac agctgcacag gccttgactt | 4980 |
| agagtgacag ccggtgtcct ggaaagcccc cagcagctgc cccagggaca tgggaagacc | 5040 |
| acgggacctc tttcactacc cacgatgacc tccgggggta tcctgggcaa aagggacaaa | 5100 |
| gagggcaaat gagatcacct cctgcagccc accactccag cacctgtgcc gaggtctgcg | 5160 |
| tcgaagacag aatggacagt gaggacagtt atgtcttgta aaagacaaga agcttcagat | 5220 |
| gggtacccca agaaggatgt gagaggtggg cgctttggag gtttgcccct cacccaccag | 5280 |
| ctgccccatc cctgaggcag cgctccatgg gggtatggtt ttgtcactgc ccagacctag | 5340 |
| cagtgacatc tcattgtccc cagcccagtg ggcattggag gtgccagggg agtcagggtt | 5400 |
| gtagccaaga cgcccccgca cggggagggt tgggaagggg gtgcaggaag ctcaacccct | 5460 |
| ctgggcacca accctgcatt gcaggttggc accttacttc cctgggatcc ccagagttgg | 5520 |
| tccaaggagg gagagtgggt tctcaatacg gtaccaaaga tataatcacc taggtttaca | 5580 |
| aatattttta ggactcacgt taactcacat ttatacagca gaaatgctat tttgtatgct | 5640 |
| gttaagtttt tctatctgtg tactttttttt taagggaaag attttaatat taaacctggt | 5700 |
| gcttctcact cacaaaaa | 5718 |

```
<210> SEQ ID NO 2
<211> LENGTH: 1106
<212> TYPE: PRT
<213> ORGANISM: Homo sapiens

<400> SEQUENCE: 2

Met Arg Leu Pro Gly Ala Met Pro Ala Leu Ala Leu Lys Gly Glu Leu
1               5                   10                  15

Leu Leu Leu Ser Leu Leu Leu Leu Glu Pro Gln Ile Ser Gln Gly
        20                  25                  30

Leu Val Val Thr Pro Pro Gly Pro Glu Leu Val Leu Asn Val Ser Ser
        35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
        115                 120                 125

Pro Asn Asp Ala Glu Glu Leu Phe Ile Phe Leu Thr Glu Ile Thr Glu
    130                 135                 140
```

```
Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
            165                 170                 175

Arg Gly Phe Ser Gly Ile Phe Glu Asp Arg Ser Tyr Ile Cys Lys Thr
            180                 185                 190

Thr Ile Gly Asp Arg Glu Val Asp Ser Asp Ala Tyr Tyr Val Tyr Arg
            195                 200                 205

Leu Gln Val Ser Ser Ile Asn Val Ser Val Asn Ala Val Gln Thr Val
            210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
                260                 265                 270

Arg Ser Ile Leu His Ile Pro Ser Ala Glu Leu Glu Asp Ser Gly Thr
            275                 280                 285

Tyr Thr Cys Asn Val Thr Glu Ser Val Asn Asp His Gln Asp Glu Lys
            290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Thr Val Leu Trp Phe Lys
                340                 345                 350

Asp Asn Arg Thr Leu Gly Asp Ser Ser Ala Gly Glu Ile Ala Leu Ser
            355                 360                 365

Thr Arg Asn Val Ser Glu Thr Arg Tyr Val Ser Glu Leu Thr Leu Val
            370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
                405                 410                 415

Val Arg Val Leu Glu Leu Ser Glu Ser His Pro Asp Ser Gly Glu Gln
                420                 425                 430

Thr Val Arg Cys Arg Gly Arg Gly Met Pro Gln Pro Asn Ile Ile Trp
            435                 440                 445

Ser Ala Cys Arg Asp Leu Lys Arg Cys Pro Arg Glu Leu Pro Pro Thr
450                 455                 460

Leu Leu Gly Asn Ser Ser Glu Glu Glu Ser Gln Leu Glu Thr Asn Val
465                 470                 475                 480

Thr Tyr Trp Glu Glu Glu Gln Glu Phe Glu Val Val Ser Thr Leu Arg
                485                 490                 495

Leu Gln His Val Asp Arg Pro Leu Ser Val Arg Cys Thr Leu Arg Asn
            500                 505                 510

Ala Val Gly Gln Asp Thr Gln Glu Val Ile Val Val Pro His Ser Leu
            515                 520                 525

Pro Phe Lys Val Val Val Ile Ser Ala Ile Leu Ala Leu Val Val Leu
            530                 535                 540

Thr Ile Ile Ser Leu Ile Ile Leu Ile Met Leu Trp Gln Lys Lys Pro
545                 550                 555                 560

Arg Tyr Glu Ile Arg Trp Lys Val Ile Glu Ser Val Ser Ser Asp Gly
```

```
              565                 570                 575
His Glu Tyr Ile Tyr Val Asp Pro Met Gln Leu Pro Tyr Asp Ser Thr
            580                 585                 590

Trp Glu Leu Pro Arg Asp Gln Leu Val Leu Gly Arg Thr Leu Gly Ser
            595                 600                 605

Gly Ala Phe Gly Gln Val Val Glu Ala Thr Ala His Gly Leu Ser His
            610                 615                 620

Ser Gln Ala Thr Met Lys Val Ala Val Lys Met Leu Lys Ser Thr Ala
625                 630                 635                 640

Arg Ser Ser Glu Lys Gln Ala Leu Met Ser Glu Leu Lys Ile Met Ser
                645                 650                 655

His Leu Gly Pro His Leu Asn Val Val Asn Leu Leu Gly Ala Cys Thr
            660                 665                 670

Lys Gly Gly Pro Ile Tyr Ile Ile Thr Glu Tyr Cys Arg Tyr Gly Asp
            675                 680                 685

Leu Val Asp Tyr Leu His Arg Asn Lys His Thr Phe Leu Gln His His
            690                 695                 700

Ser Asp Lys Arg Arg Pro Pro Ser Ala Glu Leu Tyr Ser Asn Ala Leu
705                 710                 715                 720

Pro Val Gly Leu Pro Leu Pro Ser His Val Ser Leu Thr Gly Glu Ser
                725                 730                 735

Asp Gly Gly Tyr Met Asp Met Ser Lys Asp Glu Ser Val Asp Tyr Val
            740                 745                 750

Pro Met Leu Asp Met Lys Gly Asp Val Lys Tyr Ala Asp Ile Glu Ser
            755                 760                 765

Ser Asn Tyr Met Ala Pro Tyr Asp Asn Tyr Val Pro Ser Ala Pro Glu
770                 775                 780

Arg Thr Cys Arg Ala Thr Leu Ile Asn Glu Ser Pro Val Leu Ser Tyr
785                 790                 795                 800

Met Asp Leu Val Gly Phe Ser Tyr Gln Val Ala Asn Gly Met Glu Phe
                805                 810                 815

Leu Ala Ser Lys Asn Cys Val His Arg Asp Leu Ala Ala Arg Asn Val
            820                 825                 830

Leu Ile Cys Glu Gly Lys Leu Val Lys Ile Cys Asp Phe Gly Leu Ala
            835                 840                 845

Arg Asp Ile Met Arg Asp Ser Asn Tyr Ile Ser Lys Gly Ser Thr Phe
850                 855                 860

Leu Pro Leu Lys Trp Met Ala Pro Glu Ser Ile Phe Asn Ser Leu Tyr
865                 870                 875                 880

Thr Thr Leu Ser Asp Val Trp Ser Phe Gly Ile Leu Leu Trp Glu Ile
                885                 890                 895

Phe Thr Leu Gly Gly Thr Pro Tyr Pro Glu Leu Pro Met Asn Glu Gln
            900                 905                 910

Phe Tyr Asn Ala Ile Lys Arg Gly Tyr Arg Met Ala Gln Pro Ala His
            915                 920                 925

Ala Ser Asp Glu Ile Tyr Glu Ile Met Gln Lys Cys Trp Glu Glu Lys
930                 935                 940

Phe Glu Ile Arg Pro Pro Phe Ser Gln Leu Val Leu Leu Leu Glu Arg
945                 950                 955                 960

Leu Leu Gly Glu Gly Tyr Lys Lys Lys Tyr Gln Gln Val Asp Glu Glu
                965                 970                 975

Phe Leu Arg Ser Asp His Pro Ala Ile Leu Arg Ser Gln Ala Arg Leu
            980                 985                 990
```

```
Pro Gly Phe His Gly Leu Arg Ser  Pro Leu Asp Thr Ser  Ser Val Leu
        995                 1000                 1005

Tyr Thr  Ala Val Gln Pro Asn  Glu Gly Asp Asn Asp  Tyr Ile Ile
    1010                 1015                 1020

Pro Leu  Pro Asp Pro Lys Pro  Glu Val Ala Asp Glu  Gly Pro Leu
    1025                 1030                 1035

Glu Gly  Ser Pro Ser Leu Ala  Ser Ser Thr Leu Asn  Glu Val Asn
    1040                 1045                 1050

Thr Ser  Ser Thr Ile Ser Cys  Asp Ser Pro Leu Glu  Pro Gln Asp
    1055                 1060                 1065

Glu Pro  Glu Pro Glu Pro Gln  Leu Glu Leu Gln Val  Glu Pro Glu
    1070                 1075                 1080

Pro Glu  Leu Glu Gln Leu Pro  Asp Ser Gly Cys Pro  Ala Pro Arg
    1085                 1090                 1095

Ala Glu  Ala Glu Asp Ser Phe  Leu
    1100                 1105

<210> SEQ ID NO 3
<211> LENGTH: 8089
<212> TYPE: DNA
<213> ORGANISM: Homo sapiens

<400> SEQUENCE: 3
gcggcgcgga ggctggcccg ggacgcgccc ggagcccagg gaaggaggga ggaggggagg      60
gtcgcggccg ccgccatgg ggccgggggc ccgtggccgc cgccgccgcc gtcgcccgat     120
gtcgccgcca ccgccaccgc cacccgtgcg ggcgctgccc ctgctgctgc tgctagcggg     180
gccgggggct gcagccccccc cttgcctgga cggaagcccg tgtgcaaatg gaggtcgttg     240
cacccagctg ccctcccggg aggctgcctg cctgtgcccg cctggctggg tgggtgagcg     300
gtgtcagctg gaggacccct gtcactcagg cccctgtgct ggccgtggtg tctgccagag     360
ttcagtggtg gctggcaccg cccgattctc atgccggtgc cccgtggct tccgaggccc     420 tgactgctcc ctgccagatc cctgcctcag cagcccttgt gcccacggtg cccgctgctc     480 agtgggcc gatggacgct tcctctgctc ctgcccacct ggctaccagg gccgcagctg     540
ccgaagcgac gtggatgagt gccgggtggg tgagccctgc cgccatggtg gcacctgcct     600
caacacacct ggctccttcc gctgccagt tccagctggc tacacagggc cactatgtga     660
gaaccccgcg gtgccctgtg cacccctcacc atgccgtaac gggggcacct gcaggcagag     720
tggcgacctc acttacgact gtgcctgtct tcctgggttt gagggtcaga attgtgaagt     780
gaacgtggac gactgtccag acaccgatg tctcaatggg ggacatgcg tggatggcgt     840 caacacctat aactgccagt gccctcctga gtggacaggc cagttctgca cggaggacgt     900
ggatgagtgt cagctgcagc ccaacgcctg ccacaatggg gtacctgct tcaacacgct     960 gggtggccac agctgcgtgt gtgtcaatgg ctggacaggc gagagctgca gtcagaatat    1020
cgatgactgt gccacagccg tgtgcttcca tgggggccacc tgccatgacc gcgtggcttc    1080
tttctactgt gcctgcccca tgggcaagac tggcctcctg tgtcacctgg atgacgcctg    1140
tgtcagcaac ccctgccacg aggatgctat ctgtgacaca aatccggtga acggccgggc    1200
catttgcacc tgtcctcccg gcttcacggg tgggcatgt gaccagatg tggacgagtg    1260 ctctatcggc gccaacccct gcgagcactt gggcaggtgc gtgaacacgc agggctcctt    1320
cctgtgccag tgcggtcgtg gctacactgg acctcgctgt gagaccgatg tcaacgagtg    1380
```

-continued

```
tctgtcgggg ccctgccgaa accaggccac gtgcctcgac cgcataggcc agttcacctg    1440
tatctgtatg gcaggcttca caggaaccta ttgcgaggtg gacattgacg agtgtcagag    1500
tagcccctgt gtcaacggtg gggtctgcaa ggaccgagtc aatggcttca gctgcacctg    1560
cccctcgggg ttcagcggct ccacgtgtca gctggacgtg gacgaatgcg ccagcacgcc    1620
ctgcaggaat ggcgccaaat gcgtggacca gcccgatggc tacgagtgcc gctgtgccga    1680
gggctttgag ggcacgctgt gtgatcgcaa cgtggacgac tgctcccctg acccatgcca    1740
ccatggtcgc tgcgtggatg gcatcgccag cttctcatgt gcctgtgctc ctggctacac    1800
gggcacacgc tgcgagagcc aggtggacga atgccgcagc cagccctgcc gccatggcgg    1860
caaatgccta gacctggtgg acaagtacct ctgccgctgc ccttctggga ccacaggtgt    1920
gaactgcgaa gtaacattg acgactgtgc cagcaacccc tgcaccttg gagtctgccg    1980 tgatggcatc aaccgctacg actgtgtctg ccaacctggc ttcacagggc cccttgtaa    2040 cgtggagatc aatgagtgtg cttccagccc atgcggcgag ggaggttcct gtgtggatgg    2100
ggaaaatggc ttccgctgcc tctgccgcc tggctccttg cccccactct gcctccccc    2160 gagccatccc tgtgcccatg agccctgcag tcacggcatc tgctatgatg cacctggcgg    2220
gttccgctgt gtgtgtgagc ctggctggag tggccccgc tgcagccaga gcctggcccg    2280
agacgcctgt gagtcccagc cgtgcagggc cggtgggaca tgcagcagcg atggaatggg    2340
tttccactgc acctgcccgc tggtgtcca gggacgtcag tgtgaactcc tctcccctg    2400 cacccgaac cctgtgagc atgggggccg ctgcgagtct gcccctggcc agctgcctgt    2460
ctgctcctgc cccagggct ggcaaggccc acgatgccag caggatgtgg acgagtgtgc    2520 tggcccgca ccctgtggcc ctcatggtat ctgcaccaac ctggcaggga gtttcagctg    2580
cacctgccat ggagggtaca ctggcccttc ctgcgatcag acatcaatg actgtgaccc    2640 caacccatgc ctgaacggtg gctcgtgcca agacggcgtg ggctccttt cctgctcctg    2700 cctccctggt ttcgccggcc acgatgcgc ccgcgatgtg gatgagtgcc tgagcaaccc    2760
ctgcggcccg ggcacctgta ccgaccacgt ggcctccttc acctgcacct gccgccagg    2820 ctacggaggc ttccactgcg aacaggacct gccccgactgc agcccagct cctgcttcaa    2880 tggcgggacc tgtgtggacg gcgtgaactc gttcagctgc ctgtgccgtc ccggctacac    2940
aggagcccac tgccaacatg aggcagaccc ctgcctctcg cggccctgcc tacacgggg    3000 cgtctgcagc gccgccacc ctggcttccg ctgcacctgc ctcgagagct tcacgggccc    3060
gcagtgccag acgctggtgg attggtgcag ccgccagcct tgtcaaaacg ggggtcgctg    3120
cgtccagact ggggcctatt gcctttgtcc ccctggatgg agcggacgcc tctgtgacat    3180
ccgaagcttg ccctgcaggg aggccgcagc ccagatcggg gtgcggctgg agcagctgtg    3240
tcaggcgggt gggcagtgtg tggatgaaga cagctcccac tactgcgtgt gcccagaggg    3300
ccgtactggt agccactgtg agcaggaggt ggaccctgc ttggcccagc ctgccagca    3360 tggggggacc tgccgtggct atatggggg ctacatgtgt gagtgtcttc ctggctacaa    3420
tggtgataac tgtgaggacg acgtggacga gtgtgcctcc cagccctgcc agcacggggg    3480
ttcatgcatt gacctcgtgg cccgctatct ctgctcctgt ccccaggaa cgctggggt    3540 gctctgcgag attaatgagg atgactgcgg cccaggccca ccgctggact cagggccccg    3600
gtgcctacac aatggcacct gcgtggacct ggtgggtggt ttcgctgca cctgtccccc    3660 aggatacact ggttttgcgct gcgaggcaga catcaatgag tgtcgctcag gtgcctgcca    3720
cgcggcacac acccgggact gcctgcagga cccaggcgga ggtttccgtt gcctttgtca    3780
```

```
tgctggcttc tcaggtcctc gctgtcagac tgtcctgtct ccctgcgagt cccagccatg    3840
ccagcatgga ggccagtgcc gtcctagccc gggtcctggg ggtgggctga ccttcacctg    3900
tcactgtgcc cagccgttct ggggtccgcg ttgcgagcgg gtggcgcgct cctgccggga    3960
gctgcagtgc ccggtgggcg tcccatgcca gcagacgccc cgcggccgc gctgcgcctg     4020 cccccaggg ttgtcgggac cctcctgccg cagcttcccg gggtcgccgc cggggccag     4080 caacgccagc tgcgcggccg ccccctgtct ccacggggc tcctgccgcc ccgcgccgct     4140
cgcgcccttc ttccgctgcg cttgcgcgca gggctggacc gggccgcgct gcgaggcgcc    4200
cgccgcggca cccgaggtct cggaggagcc gcggtgcccg cgcgccgcct gccaggccaa    4260
gcgcggggac cagcgctgcg accgcgagtg caacagccca ggctgcggct gggacggcgg    4320
cgactgctcg ctgagcgtgg gcgacccctg gcggcaatgc gaggcgctgc agtgctggcg    4380
cctcttcaac aacagccgct gcgaccccgc ctgcagctcg cccgcctgcc tctacgacaa    4440
cttcgactgc cacgccggtg gccgcgagcg cacttgcaac ccggtgtacg agaagtactg    4500
cgccgaccac tttgccgacg gccgctgcga ccagggctgc aacacggagg agtgcggctg    4560
ggatgggctg gattgtgcca gcgaggtgcc ggccctgctg gcccgcggcg tgctggtgct    4620
cacagtgctg ctgccgccag aggagctact gcgttccagc gccgactttc tgcagcggct    4680
cagcgccatc ctgcgcacct cgctgcgctt ccgcctggac gcgcacggcc aggccatggt    4740
cttcccttac caccggccta gtcctggctc cgaaccccgg gccgtcggg agctggcccc     4800 cgaggtgatc ggctcggtag taatgctgga gattgacaac cggctctgcc tgcagtcgcc    4860
tgagaatgat cactgcttcc ccgatgccca gagcgccgct gactacctgg gagcgttgtc    4920
agcggtggag cgcctggact tcccgtaccc actgcgggac gtgcgggggg agccgctgga    4980
gcctccagaa cccagcgtcc cgctgctgcc actgctagtg gcgggcgctg tcttgctgct    5040
ggtcattctc gtcctgggtg tcatggtggc ccggcgcaag cgcgagcaca gcaccctctg    5100
gttccctgag ggcttctcac tgcacaagga cgtggcctct ggtcacaagg gccggcggga    5160
acccgtgggc caggacgcgc tgggcatgaa gaacatggcc aagggtgaga gcctgatggg    5220
ggaggtggcc acagactgga tggacacaga gtgcccagag gccaagcggc taaaggtaga    5280
ggagccaggc atgggggctg aggaggctgt ggattgccgt cagtggactc aacaccatct    5340
ggttgctgct gacatccgcg tggcaccagc catggcactg acaccaccac agggcgacgc    5400
agatgctgat ggcatggatg tcaatgtgcg tggcccagat ggcttcaccc cgctaatgct    5460
ggcttccttc tgtgggggg ctctggagcc aatgccaact gaagaggatg aggcagatga     5520
cacatcagct agcatcatct ccgacctgat ctgccagggg gctcagcttg ggcacggac     5580 tgaccgtact ggcgagactg ctttgcacct ggctgcccgt tatgcccgtg ctgatgcagc    5640
caagcggctg ctggatgctg gggcagacac caatgcccag gaccactcag ccgcactcc     5700 cctgcacaca gctgtcacag ccgatgccca gggtgtcttc cagattctca tccgaaaccg    5760
ctctacagac ttggatgccc gcatggcaga tggctcaacg gcactgatcc tggcggcccg    5820
cctggcagta gagggcatgg tggaagagct catcgccagc catgctgatg tcaatgctgt    5880
ggatgagctt gggaaatcag ccttacactg ggctgcggct gtgaacaacg tggaagccac    5940
tttggccctg ctcaaaaatg gagccaataa ggacatgcag gatagcaagg aggagacccc    6000
cctattcctg gccgcccgcg agggcagcta tgaggctgcc aagctgctgt ggaccactt     6060 tgccaaccgt gagatcaccg accacctgga caggctgccg cgggacgtag cccaggagag    6120
```

```
actgcaccag acatcgtgc gcttgctgga tcaacccagt gggccccgca gccccccgg     6180 tccccacggc ctggggcctc tgctctgtcc tccaggggcc ttcctccctg gcctcaaagc   6240
ggcacagtcg gggtccaaga agagcaggag gccccccggg aaggcggggc tggggccgca   6300
ggggccccgg gggcggggca agaagctgac gctggcctgc ccgggccccc tggctgacag   6360
ctcggtcacg ctgtcgcccg tggactcgct ggactccccg cggcctttcg gtgggccccc   6420
tgcttcccct ggtggcttcc cccttgaggg gccctatgca gctgccactg ccactgcagt   6480
gtctctggca cagcttggtg gcccaggccg ggcgggtcta gggcgccagc cccctggagg   6540
atgtgtactc agcctgggcc tgctgaaccc tgtggctgtg ccctcgatt gggcccggct    6600 gcccccacct gcccctccag gcccctcgtt cctgctgcca ctggcgccgg accccagct    6660 gctcaaccca gggaccccg tctccccgca ggagcggccc ccgccttacc tggcagtccc    6720
aggacatggc gaggagtacc cggcggctgg ggcacacagc agcccccaa aggcccgctt    6780 cctgcgggtt cccagtgagc acccttacct gaccccatcc cccgaatccc ctgagcactg    6840
ggccagcccc tcacctccct ccctctcaga ctggtccgaa tccacgccta gcccagccac    6900
tgccactggg gccatggcca ccaccactgg ggcactgcct gcccagccac ttcccttgtc    6960
tgttcccagc tcccttgctc aggccagac ccagctgggg cccagccgg aagttacccc      7020 caagaggcaa gtgttggcct gagacgctcg tcagttctta gatcttgggg gcctaaagag    7080 accccccgtcc tgcctccttt cttctctgt ctcttccttc cttttagtct ttttcatcct     7140
cttctctttc caccaaccct cctgcatcct tgccttgcag cgtgaccgag ataggtcatc     7200
agcccagggc ttcagtcttc ctttatttat aatgggtggg ggctaccacc cacctctca     7260 gtcttgtgaa gagtctggga cctccttctt ccccacttct ctcttccctc attcctttct    7320
ctctccttct ggcctctcat ttccttacac tctgacatga atgaattatt attattttta    7380
tttttctttt ttttttttaca ttttgtatag aaacaaattc atttaaacaa acttattatt   7440 attattttt acaaaatata tatatggaga tgctccctcc ccctgtgaac ccccagtgc      7500 ccccgtgggg ctgagtctgt gggcccattc ggccaagctg gattctgtgt acctagtaca    7560
caggcatgac tggggatcccg tgtaccgagt acacgaccca ggtatgtacc aagtaggcac   7620
ccttgggcgc acccactggg gccaggggtc gggggagtgt tgggagcctc ctccccaccc    7680
cacctccctc acttcactgc attccagatg ggacatgttc catagccttg ctggggaagg    7740
gcccactgcc aactccctct gccccagccc caccccttggc catctcccctt tgggaactag  7800 ggggctgctg gtgggaaatg ggagccaggg cagatgtatg cattcctttg tgtccctgta    7860
aatgtgggac tacaagaaga ggagctgcct gagtggtact ttctcttcct ggtaatcctc    7920
tggcccagcc tcatggcaga atagaggtat ttttaggcta ttttgtaat atggcttctg     7980 gtcaaaatcc ctgtgtagct gaattcccaa gccctgcatt gtacagcccc ccactccct     8040 caccacctaa taaaggaata gttaacactc aaaaaaaaaa aaaaaaaa               8089
```

<210> SEQ ID NO 4
<211> LENGTH: 2321
<212> TYPE: PRT
<213> ORGANISM: Homo sapiens

<400> SEQUENCE: 4

Met Gly Pro Gly Ala Arg Gly Arg Arg Arg Arg Pro Met Ser
1               5                   10                  15

Pro Pro Pro Pro Pro Pro Val Arg Ala Leu Pro Leu Leu Leu Leu
            20                  25                  30

```
Leu Ala Gly Pro Gly Ala Ala Pro Pro Cys Leu Asp Gly Ser Pro
        35                  40                  45
Cys Ala Asn Gly Gly Arg Cys Thr Gln Leu Pro Ser Arg Glu Ala Ala
 50                  55                  60
Cys Leu Cys Pro Gly Trp Val Gly Glu Arg Cys Gln Leu Glu Asp
 65                  70                  75                  80
Pro Cys His Ser Gly Pro Cys Ala Gly Arg Gly Val Cys Gln Ser Ser
            85                  90                  95
Val Val Ala Gly Thr Ala Arg Phe Ser Cys Arg Cys Pro Arg Gly Phe
            100                 105                 110
Arg Gly Pro Asp Cys Ser Leu Pro Asp Pro Cys Leu Ser Ser Pro Cys
            115                 120                 125
Ala His Gly Ala Arg Cys Ser Val Gly Pro Asp Gly Arg Phe Leu Cys
            130                 135                 140
Ser Cys Pro Pro Gly Tyr Gln Gly Arg Ser Cys Arg Ser Asp Val Asp
145                 150                 155                 160
Glu Cys Arg Val Gly Glu Pro Cys Arg His Gly Gly Thr Cys Leu Asn
                165                 170                 175
Thr Pro Gly Ser Phe Arg Cys Gln Cys Pro Ala Gly Tyr Thr Gly Pro
            180                 185                 190
Leu Cys Glu Asn Pro Ala Val Pro Cys Ala Pro Ser Pro Cys Arg Asn
            195                 200                 205
Gly Gly Thr Cys Arg Gln Ser Gly Asp Leu Thr Tyr Asp Cys Ala Cys
            210                 215                 220
Leu Pro Gly Phe Glu Gly Gln Asn Cys Glu Val Asn Val Asp Asp Cys
225                 230                 235                 240
Pro Gly His Arg Cys Leu Asn Gly Gly Thr Cys Val Asp Gly Val Asn
                245                 250                 255
Thr Tyr Asn Cys Gln Cys Pro Pro Glu Trp Thr Gly Gln Phe Cys Thr
            260                 265                 270
Glu Asp Val Asp Glu Cys Gln Leu Gln Pro Asn Ala Cys His Asn Gly
            275                 280                 285
Gly Thr Cys Phe Asn Thr Leu Gly Gly His Ser Cys Val Cys Val Asn
            290                 295                 300
Gly Trp Thr Gly Glu Ser Cys Ser Gln Asn Ile Asp Asp Cys Ala Thr
305                 310                 315                 320
Ala Val Cys Phe His Gly Ala Thr Cys His Asp Arg Val Ala Ser Phe
                325                 330                 335
Tyr Cys Ala Cys Pro Met Gly Lys Thr Gly Leu Leu Cys His Leu Asp
            340                 345                 350
Asp Ala Cys Val Ser Asn Pro Cys His Glu Asp Ala Ile Cys Asp Thr
            355                 360                 365
Asn Pro Val Asn Gly Arg Ala Ile Cys Thr Cys Pro Pro Gly Phe Thr
            370                 375                 380
Gly Gly Ala Cys Asp Gln Asp Val Asp Glu Cys Ser Ile Gly Ala Asn
385                 390                 395                 400
Pro Cys Glu His Leu Gly Arg Cys Val Asn Thr Gln Gly Ser Phe Leu
                405                 410                 415
Cys Gln Cys Gly Arg Gly Tyr Thr Gly Pro Arg Cys Glu Thr Asp Val
            420                 425                 430
Asn Glu Cys Leu Ser Gly Pro Cys Arg Asn Gln Ala Thr Cys Leu Asp
            435                 440                 445
```

```
Arg Ile Gly Gln Phe Thr Cys Ile Cys Met Ala Gly Phe Thr Gly Thr
450                 455                 460
Tyr Cys Glu Val Asp Ile Asp Glu Cys Gln Ser Ser Pro Cys Val Asn
465                 470                 475                 480
Gly Gly Val Cys Lys Asp Arg Val Asn Gly Phe Ser Cys Thr Cys Pro
                485                 490                 495
Ser Gly Phe Ser Gly Ser Thr Cys Gln Leu Asp Val Asp Glu Cys Ala
            500                 505                 510
Ser Thr Pro Cys Arg Asn Gly Ala Lys Cys Val Asp Gln Pro Asp Gly
            515                 520                 525
Tyr Glu Cys Arg Cys Ala Glu Gly Phe Glu Gly Thr Leu Cys Asp Arg
530                 535                 540
Asn Val Asp Asp Cys Ser Pro Asp Pro Cys His His Gly Arg Cys Val
545                 550                 555                 560
Asp Gly Ile Ala Ser Phe Ser Cys Ala Cys Ala Pro Gly Tyr Thr Gly
                565                 570                 575
Thr Arg Cys Glu Ser Gln Val Asp Glu Cys Arg Ser Gln Pro Cys Arg
            580                 585                 590
His Gly Gly Lys Cys Leu Asp Leu Val Asp Lys Tyr Leu Cys Arg Cys
            595                 600                 605
Pro Ser Gly Thr Thr Gly Val Asn Cys Glu Val Asn Ile Asp Asp Cys
610                 615                 620
Ala Ser Asn Pro Cys Thr Phe Gly Val Cys Arg Asp Gly Ile Asn Arg
625                 630                 635                 640
Tyr Asp Cys Val Cys Gln Pro Gly Phe Thr Gly Pro Leu Cys Asn Val
                645                 650                 655
Glu Ile Asn Glu Cys Ala Ser Ser Pro Cys Gly Glu Gly Gly Ser Cys
            660                 665                 670
Val Asp Gly Glu Asn Gly Phe Arg Cys Leu Cys Pro Pro Gly Ser Leu
            675                 680                 685
Pro Pro Leu Cys Leu Pro Pro Ser His Pro Cys Ala His Glu Pro Cys
690                 695                 700
Ser His Gly Ile Cys Tyr Asp Ala Pro Gly Gly Phe Arg Cys Val Cys
705                 710                 715                 720
Glu Pro Gly Trp Ser Gly Pro Arg Cys Ser Gln Ser Leu Ala Arg Asp
                725                 730                 735
Ala Cys Glu Ser Gln Pro Cys Arg Ala Gly Gly Thr Cys Ser Ser Asp
            740                 745                 750
Gly Met Gly Phe His Cys Thr Cys Pro Pro Gly Val Gln Gly Arg Gln
            755                 760                 765
Cys Glu Leu Leu Ser Pro Cys Thr Pro Asn Pro Cys Glu His Gly Gly
770                 775                 780
Arg Cys Glu Ser Ala Pro Gly Gln Leu Pro Val Cys Ser Cys Pro Gln
785                 790                 795                 800
Gly Trp Gln Gly Pro Arg Cys Gln Gln Asp Val Asp Glu Cys Ala Gly
                805                 810                 815
Pro Ala Pro Cys Gly Pro His Gly Ile Cys Thr Asn Leu Ala Gly Ser
            820                 825                 830
Phe Ser Cys Thr Cys His Gly Gly Tyr Thr Gly Pro Ser Cys Asp Gln
            835                 840                 845
Asp Ile Asn Asp Cys Asp Pro Asn Pro Cys Leu Asn Gly Gly Ser Cys
850                 855                 860
Gln Asp Gly Val Gly Ser Phe Ser Cys Ser Cys Leu Pro Gly Phe Ala
```

```
            865                 870                 875                 880
Gly Pro Arg Cys Ala Arg Asp Val Asp Glu Cys Leu Ser Asn Pro Cys
                    885                 890                 895
Gly Pro Gly Thr Cys Thr Asp His Val Ala Ser Phe Thr Cys Thr Cys
                900                 905                 910
Pro Pro Gly Tyr Gly Gly Phe His Cys Glu Gln Asp Leu Pro Asp Cys
                915                 920                 925
Ser Pro Ser Ser Cys Phe Asn Gly Gly Thr Cys Val Asp Gly Val Asn
930                 935                 940
Ser Phe Ser Cys Leu Cys Arg Pro Gly Tyr Thr Gly Ala His Cys Gln
945                 950                 955                 960
His Glu Ala Asp Pro Cys Leu Ser Arg Pro Cys Leu His Gly Val
                965                 970                 975
Cys Ser Ala Ala His Pro Gly Phe Arg Cys Thr Cys Leu Glu Ser Phe
                980                 985                 990
Thr Gly Pro Gln Cys Gln Thr Leu Val Asp Trp Cys Ser Arg Gln Pro
                995                 1000                1005
Cys Gln Asn Gly Gly Arg Cys Val Gln Thr Gly Ala Tyr Cys Leu
        1010                1015                1020
Cys Pro Pro Gly Trp Ser Gly Arg Leu Cys Asp Ile Arg Ser Leu
        1025                1030                1035
Pro Cys Arg Glu Ala Ala Gln Ile Gly Val Arg Leu Glu Gln
        1040                1045                1050
Leu Cys Gln Ala Gly Gly Gln Cys Val Asp Glu Asp Ser Ser His
        1055                1060                1065
Tyr Cys Val Cys Pro Glu Gly Arg Thr Gly Ser His Cys Glu Gln
        1070                1075                1080
Glu Val Asp Pro Cys Leu Ala Gln Pro Cys Gln His Gly Gly Thr
        1085                1090                1095
Cys Arg Gly Tyr Met Gly Gly Tyr Met Cys Glu Cys Leu Pro Gly
        1100                1105                1110
Tyr Asn Gly Asp Asn Cys Glu Asp Asp Val Asp Glu Cys Ala Ser
        1115                1120                1125
Gln Pro Cys Gln His Gly Gly Ser Cys Ile Asp Leu Val Ala Arg
        1130                1135                1140
Tyr Leu Cys Ser Cys Pro Pro Gly Thr Leu Gly Val Leu Cys Glu
        1145                1150                1155
Ile Asn Glu Asp Asp Cys Gly Pro Gly Pro Pro Leu Asp Ser Gly
        1160                1165                1170
Pro Arg Cys Leu His Asn Gly Thr Cys Val Asp Leu Val Gly Gly
        1175                1180                1185
Phe Arg Cys Thr Cys Pro Pro Gly Tyr Thr Gly Leu Arg Cys Glu
        1190                1195                1200
Ala Asp Ile Asn Glu Cys Arg Ser Gly Ala Cys His Ala Ala His
        1205                1210                1215
Thr Arg Asp Cys Leu Gln Asp Pro Gly Gly Gly Phe Arg Cys Leu
        1220                1225                1230
Cys His Ala Gly Phe Ser Gly Pro Arg Cys Gln Thr Val Leu Ser
        1235                1240                1245
Pro Cys Glu Ser Gln Pro Cys Gln His Gly Gly Gln Cys Arg Pro
        1250                1255                1260
Ser Pro Gly Pro Gly Gly Gly Leu Thr Phe Thr Cys His Cys Ala
        1265                1270                1275
```

-continued

```
Gln Pro Phe Trp Gly Pro Arg Cys Glu Arg Val Ala Arg Ser Cys
    1280            1285                1290

Arg Glu Leu Gln Cys Pro Val Gly Val Pro Cys Gln Gln Thr Pro
    1295            1300                1305

Arg Gly Pro Arg Cys Ala Cys Pro Pro Gly Leu Ser Gly Pro Ser
    1310            1315                1320

Cys Arg Ser Phe Pro Gly Ser Pro Pro Gly Ala Ser Asn Ala Ser
    1325            1330                1335

Cys Ala Ala Ala Pro Cys Leu His Gly Gly Ser Cys Arg Pro Ala
    1340            1345                1350

Pro Leu Ala Pro Phe Phe Arg Cys Ala Cys Ala Gln Gly Trp Thr
    1355            1360                1365

Gly Pro Arg Cys Glu Ala Pro Ala Ala Ala Pro Glu Val Ser Glu
    1370            1375                1380

Glu Pro Arg Cys Pro Arg Ala Ala Cys Gln Ala Lys Arg Gly Asp
    1385            1390                1395

Gln Arg Cys Asp Arg Glu Cys Asn Ser Pro Gly Cys Gly Trp Asp
    1400            1405                1410

Gly Gly Asp Cys Ser Leu Ser Val Gly Asp Pro Trp Arg Gln Cys
    1415            1420                1425

Glu Ala Leu Gln Cys Trp Arg Leu Phe Asn Asn Ser Arg Cys Asp
    1430            1435                1440

Pro Ala Cys Ser Ser Pro Ala Cys Leu Tyr Asp Asn Phe Asp Cys
    1445            1450                1455

His Ala Gly Gly Arg Glu Arg Thr Cys Asn Pro Val Tyr Glu Lys
    1460            1465                1470

Tyr Cys Ala Asp His Phe Ala Asp Gly Arg Cys Asp Gln Gly Cys
    1475            1480                1485

Asn Thr Glu Glu Cys Gly Trp Asp Gly Leu Asp Cys Ala Ser Glu
    1490            1495                1500

Val Pro Ala Leu Leu Ala Arg Gly Val Leu Val Leu Thr Val Leu
    1505            1510                1515

Leu Pro Pro Glu Glu Leu Leu Arg Ser Ser Ala Asp Phe Leu Gln
    1520            1525                1530

Arg Leu Ser Ala Ile Leu Arg Thr Ser Leu Arg Phe Arg Leu Asp
    1535            1540                1545

Ala His Gly Gln Ala Met Val Phe Pro Tyr His Arg Pro Ser Pro
    1550            1555                1560

Gly Ser Glu Pro Arg Ala Arg Arg Glu Leu Ala Pro Glu Val Ile
    1565            1570                1575

Gly Ser Val Val Met Leu Glu Ile Asp Asn Arg Leu Cys Leu Gln
    1580            1585                1590

Ser Pro Glu Asn Asp His Cys Phe Pro Asp Ala Gln Ser Ala Ala
    1595            1600                1605

Asp Tyr Leu Gly Ala Leu Ser Ala Val Glu Arg Leu Asp Phe Pro
    1610            1615                1620

Tyr Pro Leu Arg Asp Val Arg Gly Glu Pro Leu Glu Pro Pro Glu
    1625            1630                1635

Pro Ser Val Pro Leu Leu Pro Leu Leu Val Ala Gly Ala Val Leu
    1640            1645                1650

Leu Leu Val Ile Leu Val Leu Gly Val Met Val Ala Arg Arg Lys
    1655            1660                1665
```

-continued

Arg Glu His Ser Thr Leu Trp Phe Pro Glu Gly Phe Ser Leu His
1670                    1675                    1680

Lys Asp Val Ala Ser Gly His Lys Gly Arg Arg Glu Pro Val Gly
1685                    1690                    1695

Gln Asp Ala Leu Gly Met Lys Asn Met Ala Lys Gly Glu Ser Leu
1700                    1705                    1710

Met Gly Glu Val Ala Thr Asp Trp Met Asp Thr Glu Cys Pro Glu
1715                    1720                    1725

Ala Lys Arg Leu Lys Val Glu Pro Gly Met Gly Ala Glu Glu
1730                    1735                    1740

Ala Val Asp Cys Arg Gln Trp Thr Gln His His Leu Val Ala Ala
1745                    1750                    1755

Asp Ile Arg Val Ala Pro Ala Met Ala Leu Thr Pro Pro Gln Gly
1760                    1765                    1770

Asp Ala Asp Ala Asp Gly Met Asp Val Asn Val Arg Gly Pro Asp
1775                    1780                    1785

Gly Phe Thr Pro Leu Met Leu Ala Ser Phe Cys Gly Gly Ala Leu
1790                    1795                    1800

Glu Pro Met Pro Thr Glu Glu Asp Glu Ala Asp Asp Thr Ser Ala
1805                    1810                    1815

Ser Ile Ile Ser Asp Leu Ile Cys Gln Gly Ala Gln Leu Gly Ala
1820                    1825                    1830

Arg Thr Asp Arg Thr Gly Glu Thr Ala Leu His Leu Ala Ala Arg
1835                    1840                    1845

Tyr Ala Arg Ala Asp Ala Ala Lys Arg Leu Leu Asp Ala Gly Ala
1850                    1855                    1860

Asp Thr Asn Ala Gln Asp His Ser Gly Arg Thr Pro Leu His Thr
1865                    1870                    1875

Ala Val Thr Ala Asp Ala Gln Gly Val Phe Gln Ile Leu Ile Arg
1880                    1885                    1890

Asn Arg Ser Thr Asp Leu Asp Ala Arg Met Ala Asp Gly Ser Thr
1895                    1900                    1905

Ala Leu Ile Leu Ala Ala Arg Leu Ala Val Glu Gly Met Val Glu
1910                    1915                    1920

Glu Leu Ile Ala Ser His Ala Asp Val Asn Ala Val Asp Glu Leu
1925                    1930                    1935

Gly Lys Ser Ala Leu His Trp Ala Ala Ala Val Asn Asn Val Glu
1940                    1945                    1950

Ala Thr Leu Ala Leu Leu Lys Asn Gly Ala Asn Lys Asp Met Gln
1955                    1960                    1965

Asp Ser Lys Glu Glu Thr Pro Leu Phe Leu Ala Ala Arg Glu Gly
1970                    1975                    1980

Ser Tyr Glu Ala Ala Lys Leu Leu Leu Asp His Phe Ala Asn Arg
1985                    1990                    1995

Glu Ile Thr Asp His Leu Asp Arg Leu Pro Arg Asp Val Ala Gln
2000                    2005                    2010

Glu Arg Leu His Gln Asp Ile Val Arg Leu Leu Asp Gln Pro Ser
2015                    2020                    2025

Gly Pro Arg Ser Pro Pro Gly Pro His Gly Leu Gly Pro Leu Leu
2030                    2035                    2040

Cys Pro Pro Gly Ala Phe Leu Pro Gly Leu Lys Ala Ala Gln Ser
2045                    2050                    2055

Gly Ser Lys Lys Ser Arg Arg Pro Pro Gly Lys Ala Gly Leu Gly

```
                    2060                2065                2070
Pro Gln Gly Pro Arg Gly Arg Gly Lys Lys Leu Thr Leu Ala Cys
        2075                2080                2085
Pro Gly Pro Leu Ala Asp Ser Ser Val Thr Leu Ser Pro Val Asp
        2090                2095                2100
Ser Leu Asp Ser Pro Arg Pro Phe Gly Gly Pro Pro Ala Ser Pro
        2105                2110                2115
Gly Gly Phe Pro Leu Glu Gly Pro Tyr Ala Ala Ala Thr Ala Thr
        2120                2125                2130
Ala Val Ser Leu Ala Gln Leu Gly Gly Pro Gly Arg Ala Gly Leu
        2135                2140                2145
Gly Arg Gln Pro Pro Gly Gly Cys Val Leu Ser Leu Gly Leu Leu
        2150                2155                2160
Asn Pro Val Ala Val Pro Leu Asp Trp Ala Arg Leu Pro Pro Pro
        2165                2170                2175
Ala Pro Pro Gly Pro Ser Phe Leu Leu Pro Leu Ala Pro Gly Pro
        2180                2185                2190
Gln Leu Leu Asn Pro Gly Thr Pro Val Ser Pro Gln Glu Arg Pro
        2195                2200                2205
Pro Pro Tyr Leu Ala Val Pro Gly His Gly Glu Glu Tyr Pro Ala
        2210                2215                2220
Ala Gly Ala His Ser Ser Pro Pro Lys Ala Arg Phe Leu Arg Val
        2225                2230                2235
Pro Ser Glu His Pro Tyr Leu Thr Pro Ser Pro Glu Ser Pro Glu
        2240                2245                2250
His Trp Ala Ser Pro Ser Pro Pro Ser Leu Ser Asp Trp Ser Glu
        2255                2260                2265
Ser Thr Pro Ser Pro Ala Thr Ala Thr Gly Ala Met Ala Thr Thr
        2270                2275                2280
Thr Gly Ala Leu Pro Ala Gln Pro Leu Pro Leu Ser Val Pro Ser
        2285                2290                2295
Ser Leu Ala Gln Ala Gln Thr Gln Leu Gly Pro Gln Pro Glu Val
        2300                2305                2310
Thr Pro Lys Arg Gln Val Leu Ala
        2315                2320

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
gtcactcacc cgatcacctc                                                 20

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
agcccggtgt acgagaagta                                                 20

<210> SEQ ID NO 7
```

```
<211> LENGTH: 20
<212> TYPE: DNA
<213> ORGANISM: Artificial
<220> FEATURE:
<223> OTHER INFORMATION: Primer

<400> SEQUENCE: 7
ctcccacgtg gagtcatagg                                           20

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
tgtcctagac ggacgaacct                                           20

<210> SEQ ID NO 9
<211> LENGTH: 20
<212> TYPE: DNA
<213> ORGANISM: Artificial
<220> FEATURE:
<223> OTHER INFORMATION: Primer

<400> SEQUENCE: 9
cagcaggagt gtgctgttgt                                           20

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10
cggggcagaa gagtcagaat                                           20
```